(12) United States Patent
Burdick et al.

(10) Patent No.: US 8,106,244 B2
(45) Date of Patent: Jan. 31, 2012

(54) PROCESS FOR PRODUCTION OF DELTA-9-TETRAHYDROCANNABINOL

(75) Inventors: David C. Burdick, Guilderland, NY (US); Steven J. Collier, Tanglin Park (SG); Betina Biolatto, Delmar, NY (US); Harold Meckler, Delmar, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 13/108,651

(22) Filed: May 16, 2011

(65) Prior Publication Data
US 2011/0263878 A1 Oct. 27, 2011

Related U.S. Application Data

(60) Continuation of application No. 12/626,403, filed on Nov. 25, 2009, now abandoned, which is a division of application No. 11/529,147, filed on Sep. 28, 2006, now Pat. No. 7,674,922.

(60) Provisional application No. 60/722,031, filed on Sep. 29, 2005.

(51) Int. Cl.
*C07C 35/18* (2006.01)
(52) U.S. Cl. .................................................... 568/826
(58) Field of Classification Search ................... 568/826
See application file for complete search history.

(56) References Cited

U.S. PATENT DOCUMENTS

| | | |
|---|---|---|
| 2,304,669 A | 12/1942 | Adams |
| 2,419,934 A | 5/1947 | Adams |
| 2,419,935 A | 5/1947 | Adams |
| 2,419,936 A | 5/1947 | Adams |
| 2,509,387 A | 5/1950 | Adams |
| 3,507,885 A | 4/1970 | Fahrenholtz |
| 3,562,312 A | 2/1971 | Eschenmoser et al. |
| 3,636,058 A | 1/1972 | Fahrenholtz |
| 3,734,930 A | 5/1973 | Razdan et al. |
| 3,833,616 A | 9/1974 | Petrzilka |
| 3,919,322 A | 11/1975 | Brossi et al. |
| 3,920,705 A | 11/1975 | Petrzilka |
| 4,025,516 A | 5/1977 | Razdan et al. |
| 4,054,582 A | 10/1977 | Blanchard et al. |
| 4,075,230 A | 2/1978 | Archer et al. |
| 4,102,902 A | 7/1978 | Archer et al. |
| 4,116,979 A | 9/1978 | Razdan et al. |
| 4,131,614 A | 12/1978 | Ryan |
| 4,148,809 A | 4/1979 | Day et al. |
| 4,171,315 A | 10/1979 | Ryan |
| 4,179,517 A | 12/1979 | Mechoulam et al. |
| 4,278,603 A | 7/1981 | Thakkar |
| 4,381,399 A | 4/1983 | Olsen et al. |
| 4,433,183 A | 2/1984 | Fehr et al. |
| 4,876,276 A | 10/1989 | Mechoulam et al. |
| 4,933,363 A | 6/1990 | ElSohly |
| 5,227,537 A | 7/1993 | Stoss et al. |
| 5,292,899 A | 3/1994 | Tius et al. |
| 5,338,753 A | 8/1994 | Burstein et al. |
| 5,342,971 A | 8/1994 | Herlt et al. |
| 5,389,375 A | 2/1995 | ElSohly |
| 5,440,052 A | 8/1995 | Makriyannis et al. |
| 5,521,215 A | 5/1996 | Mechoulam et al. |
| 5,538,993 A | 7/1996 | Mechoulam et al. |
| 5,605,928 A | 2/1997 | Mechoulam et al. |
| 5,635,530 A | 6/1997 | Mechoulam et al. |
| 5,872,148 A | 2/1999 | Makriyannis et al. |
| 5,932,610 A | 8/1999 | Shohami et al. |
| 6,008,383 A | 12/1999 | Elsohly et al. |
| 6,162,829 A | 12/2000 | Burstein |

(Continued)

FOREIGN PATENT DOCUMENTS

CA 2472561 A1 8/2002

(Continued)

OTHER PUBLICATIONS

"Conversion of Cannabidiol to a Product with Marihuana Activity. A Type Reaction for Synthesis of Analogous Substances. Conversion of Cannabidiol to Cannabinol," *JACS*, Communications to the Editor, 62:2245-2246 (1940).

(Continued)

*Primary Examiner* — Bernard Dentz
(74) *Attorney, Agent, or Firm* — LeClairRyan, a Professional Corporation

(57) ABSTRACT

The present invention relates to a process for preparation of a delta-9-tetrahydrocannabinol compound or derivative thereof involving treating a first intermediate compound with an organoaluminum-based Lewis acid catalyst, under conditions effective to produce the delta-9-tetrahydrocannabinol compound or derivative thereof. Another aspect of the present invention relates to a process for preparation of a cannabidiol or cannabidiolate compound involving reacting a first starting compound with a second starting compound in the presence of a metal triflate catalyst, under conditions effective to form the cannabidiol or cannabidiolate compound. The present invention also relates to a compound of the formula:

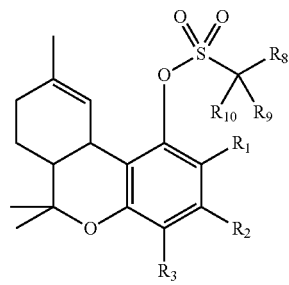

where $R_8$, $R_9$, and $R_{10}$ are the same or different and independently selected from the group consisting of H, substituted or unsubstituted alkyl, substituted or unsubstituted aryl, substituted or unsubstituted heteroaryl, or halo, with $R_1$, $R_2$, and $R_3$ defined herein.

5 Claims, No Drawings

U.S. PATENT DOCUMENTS

| | | |
|---|---|---|
| 6,274,635 B1 | 8/2001 | Travis |
| 6,331,560 B1 | 12/2001 | Shohami et al. |
| 6,355,650 B1 | 3/2002 | Burstein |
| 6,545,041 B2 | 4/2003 | Shohami et al. |
| 6,563,009 B1 | 5/2003 | Kunos et al. |
| 6,566,560 B2 | 5/2003 | Travis |
| 6,610,737 B1 | 8/2003 | Garzon et al. |
| 6,630,507 B1 | 10/2003 | Hampson et al. |
| 6,689,881 B1 | 2/2004 | Bernardelli |
| 6,730,519 B2 | 5/2004 | Elsohly et al. |
| 6,825,307 B2 | 11/2004 | Goodall |
| 6,867,335 B2 | 3/2005 | Casner et al. |
| 6,946,150 B2 | 9/2005 | Whittle |
| 6,949,582 B1 | 9/2005 | Wallace |
| 6,949,648 B2 | 9/2005 | Uchikawa et al. |
| 2002/0037923 A1 | 3/2002 | Travis |
| 2002/0049245 A1 | 4/2002 | Shohami et al. |
| 2002/0111377 A1 | 8/2002 | Stinchcomb |
| 2003/0017216 A1 | 1/2003 | Schmidt et al. |
| 2003/0158191 A1 | 8/2003 | Travis |
| 2004/0043946 A1 | 3/2004 | Popp |
| 2004/0054007 A1 | 3/2004 | Burstein et al. |
| 2004/0110827 A1 | 6/2004 | Aviv et al. |
| 2004/0143126 A1 | 7/2004 | Webster et al. |
| 2004/0225011 A1 | 11/2004 | Burstein et al. |
| 2004/0242593 A1 | 12/2004 | Moore, II et al. |
| 2004/0248970 A1 | 12/2004 | Webster et al. |
| 2004/0249174 A1 | 12/2004 | Silverberg |
| 2005/0032881 A1 | 2/2005 | Garzon et al. |
| 2005/0049298 A1 | 3/2005 | Goodwin et al. |
| 2005/0171361 A1 | 8/2005 | Goodwin et al. |
| 2005/0266108 A1 | 12/2005 | Flockhart et al. |
| 2006/0074252 A1 | 4/2006 | Souza et al. |

FOREIGN PATENT DOCUMENTS

| | | |
|---|---|---|
| DE | 101 06 024 A1 | 8/2002 |
| EP | 0 427 518 B1 | 5/1991 |
| EP | 1 186 298 B1 | 3/2002 |
| EP | 1 212 039 B1 | 6/2002 |
| EP | 1 289 517 B1 | 3/2003 |
| EP | 1 390 359 B1 | 7/2005 |
| GB | 558418 | 1/1944 |
| GB | 2 381 450 A | 5/2003 |
| GB | 2 393 182 A | 3/2004 |
| WO | WO 94/14790 | 7/1994 |
| WO | WO 95/20958 | 8/1995 |
| WO | WO 01/13886 A1 | 3/2001 |
| WO | WO 01/95899 A2 | 12/2001 |
| WO | WO 02/32420 A1 | 4/2002 |
| WO | WO 02/062782 A1 | 8/2002 |
| WO | WO 02/070506 A2 | 9/2002 |
| WO | WO 02/089945 A2 | 11/2002 |
| WO | WO 03/091189 A1 | 11/2003 |
| WO | WO 2004/026857 A2 | 4/2004 |
| WO | WO 2004/043946 A1 | 5/2004 |
| WO | WO 2004/092101 A2 | 10/2004 |
| WO | WO 2004/113320 A1 | 12/2004 |
| WO | WO 2005/100333 A1 | 10/2005 |
| WO | WO 2005/120478 A1 | 12/2005 |
| WO | WO 2006/007734 A1 | 1/2006 |
| WO | WO 2006/053766 A1 | 5/2006 |
| WO | WO 2006/063109 A2 | 6/2006 |

OTHER PUBLICATIONS

"DRONABINOL," Chemical Name: (6aR-trans)-6a,7,8,10a-tetrahydro-6,6,9-trimethyl-3-pentyl-6H-dibenzo[b,d]pyran-1-ol, Marinol (Boehringer Ingelheim, Canada, Roxane, USA, (2000).

Adams et al., "Structure of Cannabidiol. XII. Isomerization to Tetrahydrocannabinols," *JACS* 63:2209-2213 (1941).

Ágota et al., "Az Orvosszakértói Gyakorlat Kérdései," *Morphológiai es Lg. Orv. Szemle* 21:309-212 (1981), Abstract only.

Agurell et al., "A Review of Recent Studies on the Pharmacokinetics and Metabolism of Delta-l-Tetrahydrocannabinol, Cannabidiol and Cannabinol in Man," *Proc. Oxford Symp. Cannabis*, IRL Press Limited, Oxford, England, pp. 49-62 (1985).

Alessandro et al., "Metodo Rapido per L'identificazione dei Principi Attivi della <<Cannabis>> Mediante Cromatografia su Strato Sottile Circolare," *Boli. Chim. Farm.* 114:21-25 (1975), Abstract only.

Ali et al., "Chronic Marijuana Smoke Exposure in the Rhesus Monkey IV: Neurochemical Effects and Comparison to Acute and Chronic Exposure to Delta-9-Tetrahydrocannabinol (THC) in Rats," *Pharmacology Biochemistry & Behavior* 40:677-682 (1991).

Anker et al., "A New Synthesis of Olivetol," *Chem. Soc.*, pp. 311-313 (1945).

Arsenovic et al., "Formulating Aqueous Solutions of Cannabinoids Using Cyclodextrins for Effective Lowering of Intraocular Pressure," *Proceed. Int'l. Symp. Control. Rel. Bioact. Mater.* 27:606-607 (2000).

Bacigalupo et al., "Time-Resolved Fluoroimmunoassay for $\Delta^9$-Tetrahydrocannabinol As Applied to Early Discrimination of *Cannabis sativa* Plants," *J. Agric. Food Chem.* 47:2743-2745 (1999).

Baek et al., "Boron Trifluoride Etherate on Alimina—A Modified Lewis Acid Reagent. An Improved Synthesis of Cannabidiol," *Tetrahedron Lett.* 26(8):1083-1086 (1985).

Betts & Holloway, "Chromatographic Identification of Cannabis," *J. Pharm. Pharmac.* 19(Suppl.):97S-102S (1967).

Boisio, M.L., "Thin-Layer Separation of Cannabinoids from Phytosterols and Tobacco Components (Separazione su Strato Sottile di Cannabinoidi da Fitosteroli e da Componenti del Tabacco)," *1st. Med. Leg. Assicurazioni.* 24(1-4):58-60 (1976).

Bornheim & Correia, "Purification and Characterization of a Mouse Liver Cytochrome P-450 Induced by Cannabidiol," *Molecular Pharmacology* 36:377-383 (1989).

Bornheim & Correia, "Purification and Characterization of the Major Hepatic Cannabinoid Hydroxylase in the Mouse: A Possible Member of the Cytochrome P-450IIC Subfamily," *Molecular Pharmacology* 40:228-234 (1991).

Bornheim & Correia, "Selective Inactivation of Mouse Liver Cytochrome P-450IIIA by Cannabidiol," *Molecular Pharmacology* 38:319-326 (1990).

Bornheim & Grillo, "Characterization of Cytochrome P450 3A Inactivation by Cannabidiol: Possible Involvement of Cannabidiol-Hydroxyquinone as a P450 Inactivator," *Chem. Res. Toxicol.* 11:1209-1216 (1998).

Bornheim et al., "Induction and Genetic Regulation of Mouse Hepatic Cytochrome P450 by Cannabidiol," *Biochemical Pharmacology* 48(1):161-171 (1994).

Borys & Karler, "Cannabidiol and $\Delta^9$-Tetrahydrocannabinol Metabolism," *Biochemical Pharmacology* 28:1553-1559 (1979).

Braemer & Paris, "Biotransformation of Cannabinoids by a Cell Suspension Culture of *Cannibis sativa* L.," *Plant Cell Reports* 6:150-152 (1987).

Buckingham & Dahl, "The Preparation and Identification of Cannabinoid Acids and Derivatives," *Chemical Abstracts*, Abstract 90:168750b, 90:616 (1979).

Burstein et al., "Prostaglandins and Cannabis—IX. Stimulation of Prostaglandin $E_2$ Synthesis in Human Lung Fibroblasts by $\Delta^1$-Tetrahydrocannabinol," *Biochemical Pharmacology* 31(14)2361-2365 (1982).

Burstein et al., "Prostaglandins and Cannabis XIV. Tolerance to the Stimulatory Actions of Cannabinoids on Arachidonate Metabolism," *The Journal of Pharmacology and Experimental Therapeutics* 235(1):87-91 (1985).

Caddy & Fish, "A Screening Technique for Indian Hemp (*Cannabis sativa* L.)," *J. Chromatog.* 31:584-587 (1967).

Carchman et al., "The Inhibition of DNA Synthesis by Cannabinoids," *Cancer Research* 36:95-100 (1976).

Carlini et al., "Anticonvulsant Activity of Four Oxygenated Cannabidiol Derivatives," *Research Communications in Chemical Pathology and Pharmacology* 12(1):1-15 (1975).

Chan & Chaly, "A Biomimetic Synthesis of $\Delta^1$-Tetrahydrocannabinol," *Tetrahedron Lett.* 29:2935-2938 (1982).

Childers et al., "A Novel Approach to the Synthesis of the Cannabinoids," *J. Org. Chem.* 49:5276-5277 (1984).

Compton et al., "Synthesis and Pharmacological Evaluation of Amino, Azido, and Nitrogen Mustard Analogues of 10-Substituted Cannabidiol and 11- or 12- Substituted $\Delta^8$-Tetrahydrocannabinol," *J. Med. Chem.* 33:1437-1443 (1990).

Cornicelli et al., "Cannabinoids Impair the Formation of Cholesteryl Ester in Cultured Human Cells," *Arteriosclerosis* 1:449-454 (1981).
Costa et al., "Oral Anti-Inflammatory Activity of Cannabidiol, a Non-Psychoactive Constituent of Cannabis, in Acute Carrageenan-Induced Imflammation in the Rat Paw," *Naunyn-Schmiedeberg's Arch. Pharmacol.* 369:294-299 (2004).
Craigmill, A.L., "Cannabinoids and Handling-Induced Convulsions," *Research Communications in Psychology, Psychiatry and Behavior* 4(1):51-63 (1979).
Crombie et al., "Acid-Catalysed Terpenylations of Olivetol in the Synthesis of Cannabinoids," *Phytochemistry* 16:1413-1420 (1977).
Crombie et al., "Cannabinoid Acids and Esters: Miniaturized Synthesis and Chromatographic Study," *J. Chem. Soc. Perkin Trans.* 1, pp. 1243-1250 (1988).
Crombie et al., "Synthesis of Cannabinoid Methyl Esters and Acids," *J. Chem. Res.* (S):114-115 (1977).
Crombie et al., "Tetrahydrocannabinols by Terpenylation of Olivetol With (+)-trans-2- and -3-carene Epoxides," *Tetrahedron Letters* 24(30):3129-3132 (1983).
Dalterio et al., "Cannabinoids Stimulate and Inhibit Testosterone Production In vitro and In vivo," *Life Sciences* 32:605-612 (1983).
Das et al., "Cannabinoid Ligand-Receptor Signaling in the Mouse Uterus," *Proc. Natl. Acad. Sci. USA* 92:4332-4336 (1995).
Davis et al., "The Preparation and Analysis of Enriches and Pure Cannabinoids from Marihuana and Hashish," *Lloydia* 33(4):453-460 (1970).
De Faubert Maunder, M.J., "Simple Chromatography of Cannabis Constituents," Letter to the Editor, *J. Pharm. Pharmac.* 21:334-335 (1969).
Deutsch et al., "Potentiation of the Inductive Effect of Phenobarbital on Cytochrome P450 mRNAs by Cannabidiol," *Biochemical Pharmacology* 42(10):2048-2053 (1991).
Devane et al., "Determination and Characterization of a Cannabinoid Receptor in Rat Brain," *Molecular Pharmacology* 34:605-613 (1988).
Eldridge & Landfield, "Cannabinoid Interactions with Glucocorticoid Receptors in Rat Hippocampus," *Brain Research* 534:135-141 (1990).
Facci et al., "Mast Cells Express a Peripheral Cannabinoid Receptor With Differential Sensitivity to Anandamide and Palmitoylethanolamide," *Proc. Natl. Acad. Sci. USA* 92:3376-3380 (1995).
Fadda et al., "Differential Effects of THC- or CBD-rich Cannabis Extracts on Working Memory in Rats," *Neuropharmacology* 47:1170-1179 (2004).
Fichera et al., "A 3D-QSAR ?Study on the Structural Requirements for Binding to $CB_1$ and $CB_2$ Cannabinoid Receptors," *J. Med. Chem.* 43:2300-2309 (2000).
Fonseka et al., "Chromatographic Separation of Cannabinoids and Their Monooxygenated Derivatives," *Journal of Chromatography* 120:343-348 (1976).
Ford et al., "The Discriminative Stimulus Properties of Delta-9-Tetrahydrocannabinol: Generalization to Some Metabolites and Congeners," *The Cannabinoids: Chemical, Pharmacologic, and Therapeutic Aspects*, Academic Press, Inc., pp. 545-561 (1984).
Friedman, M.A., "In vivo Effects of Cannabinoids on Macromolecular Biosynthesis in Lewis Lung Carcinomas," *Cancer Biochem. Biophys.* 2:51-54 (1977).
Fluorous Technologies Incorporated, Product Application Note: Fluorous Sulfonyl Fluoride, F017074, (2000).
Fujita et al., "Studies on Cannabis (2) Examination of the Narcotic and Its Related Components in Hemps, Crude Drugs and Plant Organs by Gas-Liquid Chromatography and Thin-Layer Chromatography," *Syôkakugaku Zasshi* 21(1):37-64 (1967), Abstract only.
Gaoni & Mechoulam, "Hashish—VII. The Isomerization of Cannabidiol to Tetrahydrocannabinols," *Tetrahedron* 22:1481-1488 (1966).
Gaoni & Mechoulam, "Isolation, Structure, and Partial Synthesis of an Active Constituent of Hashish," *JACS*, Communications to the Editor, 86:1646-1647 (1964).
Gaoni & Mechoulam, "The Isolation and Structure of $\Delta^1$-Tetrahydrocannabinol and Other Neutral Cannabinoids from Hashish," *JACS* 93:217-224 (1971).

Gohda et al., "In Vivo and in Vitro Metabolism of Cannabidiol Monomethyl Ether and Cannabidiol Dimethyl Ether in the Guinea Pig: On the Formation Mechanism of Cannabielsoin-Type Metabolite from Cannabidiol," *Chem. Pharm. Bull.* 38(6):1697-1701 (1990).
Guimarães et al., "Anxiolytic Effect of Cannabidiol Derivatives in the Elevated Plus-maze," *Gen. Pharmac.* 25(1):161-164 (1994).
Handrick et al., "Hashish. Synthesis of (±)-$\Delta^1$-and $\Delta^6$-3,4-*cis*-Cannabindiols and Their Isomerization by Acid Catalysis," *J. Org. Chem.* 42(15):2563-2568 (1977).
Hanus et al., "Isolation of Cannabidiolic Acid from Turkish Variety of Cannabis Cultivated for Fiber," *Acta Universitatis Palackianae Olomucensis—Tome. 74 Facultatis Medicae*, pp. 167-172 (1975).
Haque & Poddar, "Interactions of Cannabinoids with Bovine Serum Albumin," *Bioscience Reports* 4:239-243 (1984).
Hartsel et al., "Biotransofrmation of Cannabidiol to Cannabielsoin by Suspension Cultures of *Cannabis sativa* and *Saccharum officinarum*," *Journal of Medicinal Plant Research* 48:17-19 (1983).
Harvey & Brown, "Comparative In Vitro Metabolism of the Cannabinoids," *Pharmacology Biochemistry & Behavior* 40:533-540 (1991).
Harvey & Brown, "In Vitro Metabolism of Cannabidiol in Seven Common Laboratory Mammals," *Research Communications in Substances of Abuse* 11(1 & 2):27-37 (1990).
Harvey & Brown, "In vitro Metabolism of Cannabidiol in the Rabbit: Identification of Seventeen New Metabolites Including Thirteen Dihydroxylated in the Isopropenyl Chain," *Biomedical and Environmental Mass Spectrometry* 19:559-567 (1990).
Harvey et al., "Comparative In Vivo Metabolism of $\Delta^1$-Tetrahydrocannabinol ($\Delta^1$-THC), Cannabidiol (CBD) and Cannabinol (CBN) by Several Species," *Recent Dev. Mass Spectrom. Biochem. Med., Proc. Int. Symp.*, 1:161-184 (1978).
Harvey et al., "Identification and Measurement of Cannabinoids and Their In vivo Metabolites in Liver by Gas Chromatography—Mass Spectrometry," *Advances in the Biosciences*, pp. 45-62 (1978).
Harvey et al., "Identification of Glucuronides as In vivo Liver Conjugates of Seven Cannabinoids and Some of Their Hydroxy and Acid Metabolites," *Research Communications in Chemical Pathology and Pharmacology* 16(2):265-279 (1977).
Harvey et al., "Identification of in vivo Liver Metabolites of $\Delta^1$-tetrahydrocannabinol, Cannabidiol, and Cannabinol Produced by the Guinea-Pig," *J. Pharm. Pharmacol.* 32:267-271 (1980).
Harvey et al., "Preliminary Communications. Identification of the Glucuronides of Cannabidiol and Hydroxycannabidiols in Mouse Liver," *Biochemical Pharmacology* 25:2217-2219 (1976).
Harvey, D.J., "Absorption, Distribution, and Biotransformation of the Cannabinoids," *Marihuana and Medicine*, G.G. Nahas et al., (ed.), HumanaPress Inc., Totowa, New Jersey, Chapter 2, pp. 91-103 (1999).
Harvey, D.J., "Oxidative Cleavage of the Pentyl Side-Chain of Cannabinoids," *Drug Metabolism and Disposition* 18(3):350-355 (1990).
Harvey, D.J., "Urinary Metabolites of Cannabidiol in Dog, Rat and Man and Their Identification by Gas Chromatography—mass Spectrometry," *Journal of Chromatography* 562:299-322 (1991).
Hazekamp et al., "Chromatographic and Spectroscopic Data of Cannabinoids from *Cannabis sativa* L.," *Journal of Liquid Chromatography & Related Technologies* 28:2361-2382 (2005).
Hazekamp et al., "Preparative Isolation of Cannabinoids from *Cannabis sativa* by Centrifugal Partition Chromatography," *Journal of Liquid Chromatography & Related Technologies* 27(15):2421-2439 (2004).
Hendriks et al., "Use of Amerlite XAD-2 Columns for the Separation of Cannabinoids from *Cannabis* Extracts," *Journal of Chromatography* 205:444-450 (1981).
Höppner & Menge-Hartmann, "Organspezifische Entwicklund der $\Delta$-9-Tetrahydrocannabinol (THC)- und Cannabidiol (CBD)- Konzentration während der Vegetationsperiode zweier Faserhanfsorten," *Landbauforschung Völkenrod e Heft* 2:55-64 (1996), Abstract only.
Hoton-Dorge, M., "Isolement des Principaux Constituants Phénoliques du Chanvre Indien, par Chromatographie sur Colonne et Chromatographie Préparative," *J. Pharm. Belg.* 29(5):415-422 (1974), Abstract only.

Ivančev-Tumbas et al., "GC/MS-SCAN to Follow the Fate of Crude Oil Components in Bioreactors Set to Remediate Contaminated Soil," *International Biodeterioration & Biodegradation* 54:311-318 (2004).

Jorapur et al., "A Biogenetic-Type Synthesis of Cannabifuran and Dehydrocannabifuran," *Synthetic Communications* 14(3):203-207 (1984).

Jorapur et al., "A Procedure for the Conversion of Cannabidiol Into 12β-Substituted Tetrahydrocannabinols (THC's): Synthesis of 12β-Hydroxy- $\Delta^8$-THC," *Synthetic Communications* 14(7):655-660 (1984).

Jorapur et al., "Hashish: Synthesis and Central Nervous System Activity of Some Novel Analogues of Cannabidiol and Oxepin Derivatives of $\Delta^9$-tetrahydrocannabinol," *J. Med. Chem.* 28:783-787 (1985).

Kanter et al., "Marihuana Metabolites in Urine of Man. VII. Excretion Patterns of Acidic Metabolites Detected by Sequential Thin Layer Chromatography," *Research Communications in Chemical Pathology and Pharmacology* 17(3):421-431 (1977).

Karler et al., "The Pharmacokinetic Fate of Cannabidiol and Its Relationship to Barbiturate Sleep Time," *Biochemical Pharmacology* 28:777-784 (1979).

Kawabata & Deki, "Separation of Cannabinoids by Thin-Layer Chromatography," *Kanzei Chuo Bunsekishoho* 28:103-109 (1988), Abstract only.

Kobayashi et al., "Synthesis of Cannabidiols via Alkenylation of Cyclohexenyl Monoacetate," *Organic Letters* 8(13):2699-2702 (2006).

Kojoma et al., "DNA Fingerprinting of *Cannabis sativa* Using Inter-Simple Sequence Repeat (ISSR) Amplification," *Planta Med.* 68:60-63 (2002).

Kortekaas et al., "Contribution of Extractives to Methanogenic Toxicity of Hemp Black Liquor," *Journal of Fermentation and Bioengineering* 80(4):383-388 (1995).

Kurth et al., "Hochdruckreaktionen, XIII [1] Synthese von(−) Cannabidiol at High Pressure," *Z. Naturforsch* 36b:275-276 (1981), Abstract only.

Lambert et al., "The Endocannabinoid System: Drug Targets, Lead Compounds, and Potential Therapeutic Applications," *J. Med. Chem.* 48(16):5059-5087 (2005).

Lander et al., "Total Syntheses of Cannabidiol and $\Delta^1$-Tetrahydrocannabinol Metabolites," *J. Checm. Soc. [Perkin 1]* 1:8-16 (1976).

Latta & Eaton, "Seasonal Fluctuations in Cannabinoid Content of Kansas Marijuana," *Economic Botany* 29:153-163 (1975).

Law et al., "A Novel $^{125}$I Radioimmunoassay for the Analysis of $\Delta^9$-Tetrahydrocannabinol and Its Metabolites in Human Body Fluids," *Journal of Analytical Toxicology* 8:14-18 (1984).

Lemberger et al., "Clinical Studies on the Interaction of Psychopharmacologic Agents with Marihuana," *Annals New York Academy of Sciences*, 281:219-228 (1976).

List et al., "The Efftects of $\Delta^9$-Tetrahydrocannabinol and Cannabidiol on the Metabolism of Gonadal Steroids in the Rat," *Drug Metabolism and Disposition* 5(3):268-272 (1977).

Loh et al., "Tissue Culture of *Cannabis sativa* L. and in vitro Biotransformation of Phenolics," *Z. Pflanzenphysiol. Bd.* 111.S:395-400 (1983).

Low, L.K., "Synthesis of Nitrogen Analogs of Tetrahydrocannabinol and Cannabidiol: Potential Therapeutic Agents," *Diss. Abstr. Int. B.* 40(12, Pt.1):5687 (1980) Microfilmed Dissertation.

Lu et al., "Adamantyl Cannabinoids: A Novel Class of Cannabinergic Ligands," *J. Med. Chem.* 48:4576-4585 (2005).

Lyle et al., "Synthesis and Characterization of Glucuronides of Cannabinol, Cannabidiol, $\Delta^9$-Tetrahydrocannabinol and $\Delta^8$-Tetrahydrocannabinol," *Biomedical Mass Spectrometry* 4(3):190-196 (1977).

Malkov & Kočovský, "Tetrahydrocannabinol Revisited: Synthetic Approaches Utilizing Molybdenum Catalysts," *Collect. Czech. Chem. Commun.* 66:1257-1268 (2001).

Mannila et al.., "Effects of RM-β-CD on Sublingual Bioavailability of $\Delta^9$-tetrahydrocannabinol in Rabbits," *European Journal of Pharmaceutical Sciences* 26:71-77 (2005).

Marshman et al., "A Note on the Cannabinoid Content of Jamaican ganja," *Bulletin on Narcotics* 28(4):63-68 (1976).

Martin et al., "Biotransformation of Cannabidiol in Mice. Identification of New Acid Metabolites," *Drug Metabolism and Disposition* 5(3):259-267 (1977).

Martin et al., "Dioxygenated Metabolites of Cannabidiol Formed by Rat Liver," *J. Pharm. Pharmac.* 28:603-608 (1976).

Martin et al., "Identification of Monohydroxylated Metabolites of Cannabidiol Formed by Rat Liver," *J. Pharm. Pharmac.* 28:275-279 (1976).

Masoud, A.N., "Systematic Identification of Drugs of Abuse II: TLC," *J. Pharma. Sci.* 65(11):1585-1589 (1976).

Mechoulam & Gaoni, "A Total Synthesis of dl-$\Delta^1$-Tetrahydrocannabinol, the Active Constituent of Hashish," *JACS*, Communications to the Editor, 87:3273-3275 (1965).

Mechoulam & Hanuš, "Cannabidiol: An Overview of Some Chemical and Pharmacological Aspects. Part I: Chemical Aspects," *Chemistry and Physics of Lipids* 121:35-43 (2002).

Mechoulam et al., "Aspects of Cannabis Chemistry and Metabolism," *The Pharmacology of Marihuana*, (Ed.) M.C. Braude and S. Szara Raven Press, New York, pp. 39-48 (1976).

Mechoulam et al., "Cannabinoids in Models of Chronic Inflammatory Conditions," *Phytochemistry Reviews* 4:11-18 (2005).

Mechoulam et al., "Hashish. IV. Isolation and Structure of Annabinolic, Cannabidiolic, and Cannabigerolic Acids," *Tetrahedron* 21(5):1223-1229 (1965).

Mechoulam et al., "Recent Advances in the Chemistry and Biochemistry of Cannabis," *Chem. Rev.* 76(1):75-112 (1976).

Mechoulam et al., "Syntheses of $\Delta^1$-Tetrahydrocannabinol and Related Cannabinoids," *JACS* 94:6159-6165 (1972).

Menge-Hartmann & Höppner, "Brakteentrichome und ihre Beziehung zum Cannabinoidgehalt zweier Faserhanfsorten," *Landbauforschung Völkenrod e Heft* 2:49-54 (1996), Abstract only.

Nilsson et al., "Two Cannabidiol Metabolites Formed by Rat Liver," Letters to the Editor, *J. Pharm. Pharmac.* 25:486-487 (1973).

Novotny et al., "Analysis of Marijuana Samples from Different Origins by High-Resolution Gas-Liquid Chromatography for Forensic Application," *Anal. Chem.* 48(1):24-29 (1976).

Nye et al., "High-Affinity Cannabinoid Binding Sites in Brain Membranes Labeled with [$^3$H]-5'-Trimethylammonium $\Delta^8$-Tetrahydrocannabinol," *Journal of Pharmacology and Experimental Therapeutics* 234(3):784-791 (1985).

Nye et al., "Labelling of a Cannabinoid Binding Site in Brain with a [$^3$H]quarternary Ammonium Analogue of Delta-8-THC," *Proc. Oxford Symp. Cannabis*, IRL Press Limited, Oxford, England, pp. 253-262 (1985).

Ohlsson et al., "Detection and Quantification of Tetrahydrocannabinol in Blood Plasma," *NIDA Res. Monogr.* 7:48-63 (1976).

Ohlsson et al., "Single Dose Kinetics of Cannabidiol in Man," *The Cannabinoids: Chemical, Pharmacologic, and Therapeutic Aspects*, Academic Press, Inc., pp. 219-225 (1984).

Ohlsson et al., "Single-Dose Kinetics of Deuterium-Labelled Cannabidiol in Man After Smoking and Intravenous Administration," *Biomedical and Environmental Mass Spectrometry* 13:77-83 (1986).

Onaivi et al., "Pharmacological Characterization of Cannabinoids in the Elevated Plus Maze," *Journal of Pharmacology and Experimental Therapeutics* 253(3):1002-1009 (1990).

Ooi & Maruoka, "Product Subclass4; Aluminum Alkoxides and Phenoxides," *Science of Synthesis; Houben-Weyl Methods of Molecular Transformations* 7:131-195 (2004).

Papahatjis et al., "Novel 1',1'-Chain Substituted $\Delta^9$-Tetrahydrocannabinols," *Bioorganic & Medicinal Chemistry Letters* 12:3583-3586 (2002).

Papahatjis et al., "Pharmacophoric Requirements for the Cannabinoid Side Chain. Probing the Cannabinoid Receptor Subsite at C1," *J Med. Chem.* 46:3221-3229 (2003).

Petrzilka et al., "123. Synthese von Haschisch-Inhaltsstoffen," *Helv. Chim. Acta* 52:1102-1134 (1969), Abstract only.

Petrzilka et al., "74. Synthese and Chiralität des (−)-Cannabidiols," *Helv. Chim. Acta* 50:719-723 (1967), Abstract only.

Pijlman et al., "Strong Increase in Total Delta-THC in Cannabis Preparations Sold in Dutch Coffee Shops," *Addiction Biology* 10:171-180 (2005).

Quarles et al., "Toxicology of Marijuana: Conditions for Conversion of Cannabidiol to THC Upon Smoking," *Clinical Toxicology* 6(2):211-216 (1973).

Rannazzisi, J.T., "Department of Justice. Drug Enforcement Administration. Manufacturer of Controlled Substances; Notice of Application," *Federal Register* 70(242):75219 (Dec. 19, 2005).

Razdan et al., "Hashish. A Simple One-Step Synthesis of (–)-$\Delta^1$-Tetrahydrocannabinol (THC) from *p*-Mentha-2,8-dien-1-ol and Olivetol," *JACS* 96(18):5860-5865 (1974).

Razdan, R.K., "The Total Synthesis of Cannabinoids," vol. 4 (ed. John Apsimon) pp. 185-262 (1981).

Reggio et al., "The Design, Synthesis and Testing of Desoxy-CBD: Further Evidence for a Region of Steric Interference at the Cannabinoid Receptor," *Life Sciences* 56(23/24):2025-2032 (1995).

Reichman et al., "Effects of $\Delta^1$-Tetrahydrocannabinol on Prostaglandin Formation in Brain," *Molecular Pharmacology* 32:686-690 (1987).

Reiss, J., "Kurze Mitteilungen/ShortCommunications. Dünnschichtchromatographische Auftrennung der Inhaltsstoffe von Haschisch auf Kieselgel-Fertigplatten," *Arch. Toxikol.* 29:365-366 (1972), Abstract only.

Repetto et al., "Separation of Cannabinoids," *Bulletin on Narcotics* 28(4):69-74 (1976).

Rickards et al., "Synthesis of (–)-delta9-6a, 10a-trans-Tetrahydrocannabinol. Boron Trifluoride Catalyzed Arylation by a Homocuprate," *Journal of Organic Chemistry* 49:572-73 (1984).

Robertson et al., "Biotransformation of Cannabinoids by *Syncephalastrum racemosum*," *Biomedical Mass Spectrometry* 2:266-271 (1975).

Robinson, A.E., "Recovery of Cannabis Constituents from the Hands at Autopsy," *Bulletin on Narcotics* 23(3):37-40 (1971).

Rothschild et al., "Storage of Cannabinoids by *Arctia caja* and *Zonocerus elegans* Fed on Chemically Distinct Strains of *Cannabis sativa*," *Nature* 266:650-651 (1977).

Sacerdote et al., "The Nonpsychoactive Component of Marijuana Cannabidiol Modulates Chemotaxis and IL-10 and IL-12 Production of Murine Macrophages Bith In vivo and In vitro," *Journal of Neuroimmunology* 159:97-105 (2005).

Samara & Bialer, "Pharmacokinetics of Cannabidiol After Intravenous Administration in Dogs," *Proc. Eur. Congr. Biopharm. Pharmacokinet.* 228-236 (1987).

Samara et al., "Identification of Glucose Conjugates as Major Urinary Metabolites of Cannabidiol in the Dog," *Xenobiotica* 20(2):177-183 (1990).

Samara et al., "Identification of Urinary Metabolites of Cannabidiol in the Dog," *Drug Metabolism and Disposition* 18(5):571-579 (1990).

Samara et al., "Metabolism of Cannabidiol by the Rat," *European Journal of Drug Metabolism and Pharmacokinetics* 16(4):305-313 (1991).

Samara et al., "Pharmacokinetics of Cannabidiol in Dogs," *Drug Metabolism and Disposition* 16(3):469-472 (1988).

Schmetzer et al., "Structure-Activity Relationships of Cannabinoids: A Joint CoMFA and Pseudoreceptor Modelling Study," *Journal of Computer-Aided Molecular Design* 11:278-292 (1997).

Shah, V.J., "Synthesis of Cannabidiol Stereoisomers and Analogs as Potential Anticonvulsant Agents," *Diss. Abstr. Int. B.* 50(2):580 (1988) Microfilmed Dissertation.

Shani et al., "Cannabielsoic Acids. Isolation and Synthesis by a Novel Oxidative Cyclization," *Tetrahedron* 30(15):2437-2446 (1974).

Showalter et al., "Evaluation of Binding in a Transfected Cell Line Expressing a Peripheral Cannabinoid Receptor (CB2): Identification of Cannabinoid Receptor Subtype Selective Ligands," *JPET* 278:989-999 (1996).

Shulgin, A.T., "Recent Developments in Cannabis Chemistry," *Journal of Psychedelic Drugs* 2(1):397-415 (1971).

Siemens et al., "Characterization of Blood Disappearance and Tissue Distribution of [$^3$H]cannabidiol," *Biochemical Pharmacology* 29:462-464 (1980).

Sirikantaramas et al., "Tetrahydrocannabinolic Acid Synthase, the Enzyme Controlling Marijuana Psychoactivity, is Secreted Into the Storage Cavity of the Glandular Trichomes," *Plant Cell Physiol.* 46(9):1578-1582 (2005).

Smith, R.N., "High-Pressure Liquid Chromatography of Cannabis Identification of Separated Constituents," *Journal of Chromatography* 115:101-106 (1975).

Spronck et al., "Inhibition of Prostaglandin Biosynthesis by Derivatives of Olivetol Formed Under Pyrolysis of Cannabidiol," *Biochemical Pharmacology* 27:607-608 (1978).

Stefanidou et al., "The Cannabinoid Content of Marihuana Samples Seized in Greece and Its Forensic Application," *Forensic Science International* 95:153-162 (1998).

Stott & Guy, "Cannabinoids for the Pharmaceutical Industry," *Euphytica* 140:83-93 (2004).

Tanaka & Shoyama, "Monoclonal Antibody Against Tetrahydrocannabinolic Acid Distinguishes *Cannabis sativa* Samples From Different Plant Species," *Forensic Science International* 106:135-146 (1999).

Tanaka et al., "Cannabis 25$^1$, Biotransformation of Cannabidiol and Cannabidiolic Acid by *Pinellia ternata* Tissue Segments," *Plant Cell Reports* 15:819-823 (1996).

Tchilibon & Mechoulam, "Synthesis of a Primary Metabolite of Cannabidiol," *Organic Letters* 2(21):3301-3303 (2000).

Teale et al., "Plasma Cannabinoids Measured by Radioimmunoassay in Rabbits After Intravenous Injection of Tetrahydrocannabinol, 11-Hydroxy-Tetrahydrocannabinol, Cannabinol and Cannabidiol," *Research Communications in Chemical Pathology and Pharmacology* 11(2):339-342 (1975).

Tewari & Sharma, "Separation and Identification of Cannabinoids from *Cannabis indica* L. by Thin Layer Chromatography," *Pharmazie* 34(1):54 (1979).

Thomas et al., "Comparative Receptor Binding Analyses of Cannabinoid Agonist and Antagonists," *JPET* 285(1):285-292 (1998).

Tilak & Zimmerman, "Effects of Cannabinoids on Macromolecular Synthesis on Isolated Spermatogenic Cells," *Pharmacology* 29:343-350 (1984).

Tius, M.A., "Stereospecific Cannabinoid Synthesis: The Application of New Techniques to a Classical Problem," *in* Studies in Natural Products Chemistry, Atta-ur-Rahman (Ed.), vol. 19, pp. 185-244 (1997).

Turner & Hadley, "Constituents of *Cannabis sativa* L. III: Clear and Discrete Separation of Cannabidiol and Cannabichromene," *J. Pharm. Sci.* 62(7):1083-1086 (1973).

Turner et al., "Constituents of *Cannabis sativa* L. VIII: Possible Biological Application of a New Method to Separate Cannabidiol and Cannabichromene," *Journal of Pharmaceutical Science* 64(5):810-814 (1975).

Turner et al., "Trichomes and Cannabinoid Content of Developing Leaves and Bracts of *Cannabis sativa* L. (*Cannabaceae*)," *Amer. J. Bot.* 67(10):1397-1406 (1980).

Uliss et al., "Hashish. Importance of the Phenolic Hydroxyl Group in Tetrahydrocannabinols," *J. Med. Chem.* 18(2):213-215 (1975).

Usami et al., "A Cytochrome P450 Enzyme Responsible for Carbon Monoxide Formation by Cannabidiol in Mouse Hepatic Microsomes," *Research Communications in Alcohol and Substances of Abuse* 20(1 & 2):69-77 (1999).

Usami et al., "Formation of Carbon Monoxide During Mouse Hepatic Microsomal Oxidative Metabolism of Cannabidiol; Identification and Determination," *Biol. Pharm. Bull.* 18(4):529-535 (1995).

Usami et al., "Synthesis and Pharmacological Evaluation in Mice of Halogenated Cannabidiol Derivatives," *Chem. Pharm. Bull.* 47(11):1641-1645 (1999).

Vaillancourt & Albizati, "A One-Step Method for the $\alpha$-Arylation of Camphor. Synthesis of (–)-Cannabidiol and (–)-Cannabidiol Dimethyl Ether," *J. Org. Chem.* 57:3627-3631 (1992).

Valentine et al., "High-Pressure Liquid Chromatographic-Mass Spectrometric Determination of $\Delta^9$-Tetrahydrocannabinol in Human Plasma Following Marijuana Smoking," *J. Pharma. Sci.* 66(9):1263-1266 (1977).

Van Drooge et al., "Spray Freeze Drying to Produce a Stable $\Delta^9$-tetrahydrocannabinol Containing Inulin-Based Solid Dispersion Powder Suitable for Inhalation," *European Journal of Pharmaceutical Sciences* 26:231-240 (2005).

Veress et al., "HPLC Analysis of Cannabinoids Using Amino Bonded Stationary Phase Column," *Chromatography '87*, H. Kalász & L.S. Ettre (Eds.), Budapest pp. 481-493 (1988).

Vree et al., "Identification of Cannabivarins in Hashish by a New Method of Combined Gas Chromatography-Mass-Spectrometry," *Clin. Chim. Acta* 34:365-372 (1971).

Watanabe et al., "Formation of Similar Species to Carbon Monoxide During Hepatic Microsomal Metabolism of Cannabidiol on the Basis of Spectral Interaction with Cytochrome P-450," *Biochemical Pharmacology* 37(24):4719-4726 (1988).

White & Tansik, "Effects of $\Delta^9$-Tetrahydrocannabinol and Cannabidiol on Phospholipase and Other Enzymes Regulating Arachidonate Metabolism," *Prostaglandins and Medicine* 4:409-411 (1980).

Yamamoto et al., "A Novel Metabolite, An Oxepin Formed from Cannabidiol with Guinea-Pig Hepatic Microsomes," *J. Pharm. Pharmacol.* 47:683-686 (1995).

Yamamoto et al., "Identification of Cannabielsoin, a New Metabolite of Cannabidiol Formed by Guinea-Pig Hepatic Microsomal Enzymes, and Its Pharmacological Activity in Mice," *J. Pharmacobio-Dyn.* 11:833-838 (1988).

Yamamoto et al., "Mechanism of Biological Formation of Cannabielsoin from Cannabidiol in the Guinea-Pig, Mouse, Rat and Rabbit," *J. Pharmacobio-Dyn.* 12:488-494 (1989).

Yamamoto, I., "Metabolic Activation of Major Cannabinoids," *Curr. Top. Forensic Sci.*, Proc. Meet. Int. Assoc. Forensic S, pp. 293-295 (1997).

Yamamoto, I., "Metabolism of Cannabinoids—Pharmacological and Toxilogical Significance," *Japanese Journal of Forensic Toxicology* 12(2):96-99 (1994), Abstract only.

Yoo et al., "Mammary Excretion of Cannabidiol in Rabbits After Intravenous Administration," *J. Pharm. Pharmacol.* 46:926-928 (1994).

*Acta Pharmaceutical Hungarica* 64(1):22-25 (1994), Abstract only.
*Bioorganic and Medicinal Chemistry Letters* 6(6):671-674 (1996), Abstract only.
*Bioorganic and Medicinal Chemistry Letters* 11(13):1671-1673 (2001), Abstract only.
*Canadian Journal of Chemistry* 74(9):1638-1648 (1996), Abstract only.
*Canadian Journal of Chemistry* 63(10):2589-2596 (1985), Abstract only.
*Canadian Journal of Chemistry* 66(12):3070-3076 (1988), Abstract only.
*Canadian Journal of Chemistry* 68(8):1450-1455 (1990), Abstract only.
*Drug Development Research* 54(2):75-87 (2001), Abstract only.
European Patent No. 751134 (Jan. 2, 1997), Abstract only.
European Patent No. 985662 (Mar. 15, 2000), Abstract only.
German Patent No. 289265 (Apr. 25, 1991), Abstract only.
German Patent No. 289266 (Apr. 25, 1991), Abstract only.
Japanese Patent No. 2000336081 (Dec. 5, 2000), Abstract only.
*Journal fuer Praktische Chemie (Leipzig)* 329(6):1137-1142 (1987), Abstract only.
*Journal fuer Praktische Chemie (Leipzig)* 329(6):1143-1146 (1987), Abstract only.
*Journal of Medicinal Chemistry* 30(6):1040-1044 (1987), Abstract only.
*Journal of Medicinal Chemistry* 30(9):1682-1686 (1987), Abstract only.
*Journal of Medicinal Chemistry* 31(10):1978-1983 (1988), Abstract only.
*Journal of Medicinal Chemistry* 32(7):1467-1471 (1989), Abstract only.
*Journal of Medicinal Chemistry* 37(17):2735-2753 (1994), Abstract only.
*Journal of Medicinal Chemistry* 44(25):4393-4403 (2001), Abstract only.
*Journal of Organic Chemistry* 50(12):2158-2165 (1985), Abstract only.
*Journal of Organic Chemistry* 52(7):1305-1309 (1987), Abstract only.
*Journal of Organic Chemistry* 52(11):2285-2292 (1987), Abstract only.
*Journal of Organic Chemistry* 53(20):4667-4675 (1988), Abstract only.
*Journal of Photochemistry and Photobiology, A: Chemistry* 69(3):313-323 (1992), Abstract only.
*Journal of the American Chemical Society* 110(18):6153-6162 (1988), Abstract only.
*Journal of the American Chemical Society* 111(14):5472-5474 (1989), Abstract only.
*Journal of the Chemical Society, Chemical Communications* 9:654-656 (1987), Abstract only.
*Journal of the Chemical Society, Chemical Communications* 21:1468-1469 (1985), Abstract only.
*Journal of the Chemical Society, Perkin Transactions 1: Organic and Bio-Organic Chemistry* 6:1581-1587 (1991), Abstract only.
*Journal of the Chemical Society, Perkin Transactions 1: Organic and Bio-Organic Chemistry* 22:2855-2860 (1995), Abstract only.
*Journal of the Chemical Society, Perkin Transactions 1: Organic and Bio-Organic Chemistry* 20:3029-3038 (1999), Abstract only.
*Liebigs Annalen der Chemie* 6:495-498 (1987), Abstract only.
*Organic Letters* 2(18):2729-2731 (2000), Abstract only.
*Organic Letters* 3(9):1359-1362 (2001), Abstract only.
PCT Application Publication No. 95/09169 (Apr. 6, 1995), Abstract only.
PCT Application Publication No. 99/50260 (Oct. 7, 1999), Abstract only.
PCT Application Publication No. 99/67228 (Dec. 29, 1999), Abstract only.
*Perkin 1* 24:4339-4346 (2000), Abstract only.
*Phosphorus and Sulfur and the Related Elements* 32(3-4):91-97 (1987), Abstract only.
*Phosphorus and Sulfur and the Related Elements* 32(3-4):99-103 (1987), Abstract only.
*Sulfur Letters* 24(3):137-145 (2000), Abstract only.
*Synthesis* 3:246-248 (1988), Abstract only.
*Synthesis* 10:760-763 (1988), Abstract only.
*Synlett* 7:1103-1105 (1999), Abstract only.
*Tetrahedron* 54(1/2):45-64 (1998), Abstract only.
*Tetrahedron* 56(29):5147-5155 (2000), Abstract only.
*Tetrahedron* 56(37):7163-7171 (2000), Abstract only.
*Tetrahedron* 56(47):9181-9193 (2000), Abstract only.
*Tetrahedron Letters* 26(2):157-160 (1985), Abstract only.
*Tetrahedron Letters* 29(44):5595-5598 (1988), Abstract only.
*Tetrahedron Letters* 36(50):9197-9200 (1995), Abstract only.
*Tetrahedron Letters* 41(42):8183-8187 (2000), Abstract only.

PROCESS FOR PRODUCTION OF DELTA-9-TETRAHYDROCANNABINOL

This application is a continuation of U.S. patent application Ser. No. 12/626,403, filed Nov. 25, 2009 now abandoned, which is a division of U.S. patent application Ser. No. 11/529,147, filed Sep. 28, 2006, now U.S. Pat. No. 7,674,922, issued Mar. 9, 2010, which claims the benefit of U.S. Provisional Patent Application Ser. No. 60/722,031, filed Sep. 29, 2005, which are hereby incorporated by reference in their entirety.

FIELD OF THE INVENTION

The present invention relates to processes for preparation of (−)-trans-delta-9-tetrahydrocannabinol, intermediate compounds thereof, and derivative compounds thereof.

BACKGROUND OF THE INVENTION

In the years since the appearance of Razdan's groundbreaking review on the synthesis of cannabinoids, research activity has continued apace (Razdan, in ApSimon, ed., *The Total Synthesis of Natural Products*, Vol. 4, pp. 185-262, New York, N.Y.: Wiley and Sons (1981); Huffman et al., *Current Med. Chem.*, 3:101-116 (1996)). The interest which this area engenders is due in part to the challenge which the structures pose to the synthetic organic chemist, and also because of the diverse and useful pharmacological activities which many of these materials express. The chemical structures of the naturally occurring tricyclic cannabinoids, typified by delta-9-tetrahydrocannabinol (delta-9-THC), are very simple: there are only two stereogenic carbon atoms, two carbocycles and the dihydrobenzopyran ring. The functionality is in most cases limited to the phenolic C1 hydroxyl and to one or two oxygen-bearing functional groups. One would be justified in questioning whether this class of compounds is of sufficient complexity to continue to interest the organic chemist. The difficulties of the synthesis belie the simplicity of the structure, and are due, at least in part, to the following: (a) the materials are typically non-crystalline, and are often quite difficult or impossible to separate and purify without recourse to HPLC; (b) the aromatic portion of the molecule is very sensitive to oxidation, particularly in the presence of base or transition metals (see Hodjat-Kashani et al., *Heterocycles*, 24:1973-1976 (1986)); and (c) the delta-9-unsaturation is thermodynamically disfavored relative to delta-8-unsaturation. There is also no general method by which to favor delta-9-unsaturation kinetically.

Interest in the pharmacology of these materials goes back many thousands of years (Abel, *Marijuana: The First Twelve Thousand Years*, pp. 11-12, New York and London: Plenum Press (1980)). Herodotus' account of the Scythians' use of *Cannabis sativa* as an intoxicant makes it clear that the psychotropic properties of the producing plant were recognized since antiquity (Herodotus, *The Histories*, Book IV, pp. 295, Penguin Books, Ltd., Middlesex (1972)). In addition to uses as anaesthetics, spasmolytics, and hypnotics, cannabinoids have been used to combat emesis and nausea induced by cancer chemotherapy, and also in the treatment of glaucoma. In recent times, cannabinoids have achieved a certain notoriety due to their abuse potential. A significant portion of the synthetic effort has been directed toward the preparation of some of the oxygenated human urinary metabolites of delta-9-THC for use in forensic science as analytical standards for the detection of marijuana use.

Several developments have contributed to the current resurgence in interest in this area. The identification of the first cannabinoid receptor (CB1) in rat brain (Devane et al., *Mol. Pharmacol.*, 34:605-613 (1988)) was a major advance. The identification of a second, peripheral, receptor subtype in splenocytes (CB2) (Munro et al., *Nature*, 365:61-65 (1993)), as well as the discovery of arachidonylethanolamine (anandamide) as the endogenous ligand for CB1 (Devane et al., *Science*, 258:1946-1949 (1992)), has made the story much more interesting. Involvement of the pharmaceutical industry has resulted in synthesis and evaluation of large numbers of analogs, and in the discovery of the first receptor antagonist.

The present invention is directed to overcoming the above-noted deficiencies in the art.

SUMMARY OF THE INVENTION

The present invention relates to a process for preparation of a product compound of the formula:

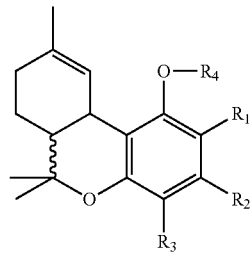

where:
- $R_1$ is H, substituted or unsubstituted alkyl, carboxylic ester, or acyl;
- $R_2$ is H, OH, protected hydroxyl, substituted or unsubstituted alkyl, alkenyl, alkynyl, acyl, aryl, or heteroaryl;
- $R_3$ is H, substituted or unsubstituted alkyl, carboxylic ester, or acyl; and
- $R_4$ is H, substituted or unsubstituted alkyl, silyl, hetero-substituted or unsubstituted acyl, alkylsulfonyl, arylsulfonyl, alkylphosphoryl, or arylphosphoryl.

The process involves treating a first intermediate compound of the formula:

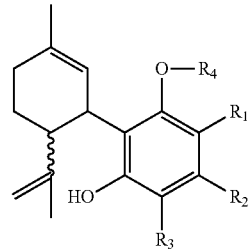

with an organoaluminum-based Lewis acid catalyst, under conditions effective to produce the product compound.

Another aspect of the present invention relates to a process for preparation of a product compound of the formula:

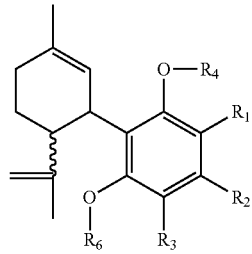

where:
R₁ is H, substituted or unsubstituted alkyl, carboxylic ester, or acyl;
R₂ is H, OH, protected hydroxyl, substituted or unsubstituted alkyl, alkenyl, alkynyl, acyl, aryl, or heteroaryl;
R₃ is H, substituted or unsubstituted alkyl, carboxylic ester, or acyl;
R₄ is H, substituted or unsubstituted alkyl, silyl, hetero-substituted or unsubstituted acyl, alkylsulfonyl, arylsulfonyl, alkylphosphoryl, or arylphosphoryl; and
R₆ is H, substituted or unsubstituted alkyl, silyl, hetero-substituted or unsubstituted acyl, alkylsulfonyl, arylsulfonyl, alkylphosphoryl, or arylphosphoryl.

The process involves reacting a first starting compound of the formula:

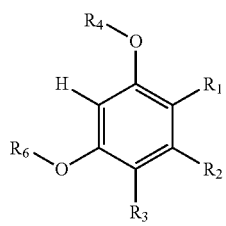

with a second starting compound of the formula:

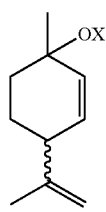

where X=H, alkyl, acyl, silyl, aryl, heteroaryl, sulfonyl, phosphoryl, or phosphinyl, in the presence of a metal triflate catalyst, under conditions effective to form the product compound.

Yet another aspect of the present invention relates to a process for preparation of a product compound of the formula:

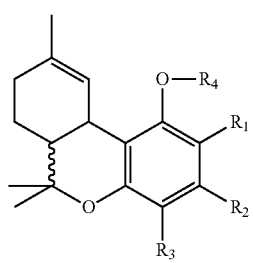

where:
R₁ is H, substituted or unsubstituted alkyl, carboxylic ester, or acyl;
R₂ is H, OH, protected hydroxyl, substituted or unsubstituted alkyl, alkenyl, alkynyl, acyl, aryl, or heteroaryl;
R₃ is H, substituted or unsubstituted alkyl, carboxylic ester, or acyl; and
R₄ is SO₂R₅, wherein R₅ is substituted or unsubstituted alkyl.

The process involves reacting a first intermediate compound of the formula:

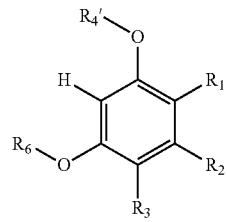

wherein:
R₄' is H, substituted or unsubstituted alkyl, silyl, hetero-substituted or unsubstituted acyl, alkylsulfonyl, arylsulfonyl, alkylphosphoryl, or arylphosphoryl,
R₆ is H, substituted or unsubstituted alkyl, silyl, hetero-substituted or unsubstituted acyl, alkylsulfonyl, arylsulfonyl, alkylphosphoryl, or arylphosphoryl,
wherein at least one of R₄' and R₆ must be H;
with a first compound of the formula:

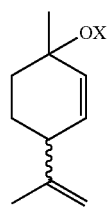

where X=H, alkyl, acyl, silyl, aryl, heteroaryl, sulfinyl, sulfonyl, phosphoryl, or phosphinyl, in the presence of a metal triflate catalyst, under conditions effective to form a second intermediate compound of the formula:

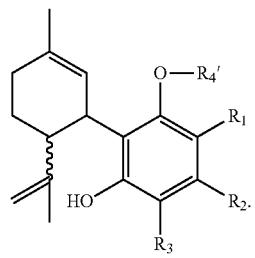

Next, the second intermediate compound is treated with an organoaluminum-based Lewis acid catalyst, under conditions effective to produce a third intermediate compound of the formula:

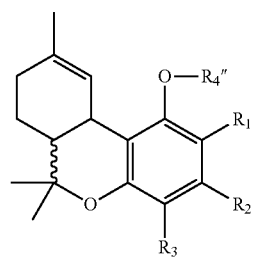

wherein $R_4''$=H. Then, the third intermediate compound is reacted with a substituted or unsubstituted alkylsulfonyl halide, alkylsulfonyl anhydride, alkylsulfonyl mixed anhydride, alkylsulfonyl ester, or alkylsulfonic acid, under conditions effective to produce the product compound.

The present invention also relates to a compound of the formula:

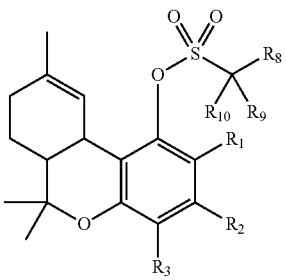

where:
$R_1$ is H, substituted or unsubstituted alkyl, carboxylic ester, or acyl;
$R_2$ is H, OH, protected hydroxyl, substituted or unsubstituted alkyl, alkenyl, alkynyl, acyl, aryl, or heteroaryl;
$R_3$ is H, substituted or unsubstituted alkyl, carboxylic ester, or acyl;
$R_8$, $R_9$, and $R_{10}$ are the same or different and independently selected from the group consisting of H, substituted or unsubstituted alkyl, substituted or unsubstituted aryl, substituted or unsubstituted heteroaryl, or halo; and
$R_8$ and $R_9$; $R_8$ and $R_{10}$; or $R_9$ and $R_{10}$; or $R_8$, $R_9$, and $R_{10}$ can together result in the formation of a cyclic moiety.

The condensation of olivetol or an olivetolate ester with menthadienol in the presence of Lewis acids has been known in the prior art. However, the reactions were plagued by problems with poor selectivity and subsequent conversion of the desired products to cyclized derivatives with little control. For example, boron trifluoride etherate ($BF_3OEt_2$) gives poor control over the reactions as it is difficult to stop at cannabidiol and the cyclization to delta-9-THC with further isomerization to delta-8-THCs is a common problem. The use of less reactive Lewis acids, such as $MgBr_2$, is not favorable due to their poor reactivity. As the scale of these reactions increases, the control over the process becomes more difficult, due to the short reaction times needed. By using metal triflate catalysts, the reactions of the present invention proceed under mild conditions with practically no overreaction to cyclized products. In addition, in the case of olivetol, both the desired cannabidiol and an unwanted isomer, abn-cannabidiol, are formed when $BF_3OEt_2$ is used as catalyst. However, the combination of a metal triflate catalyst, and the slow addition of menthadienol (preferably less than one equivalent) gives improved ratios of cannabidiol to abn-cannabidiol. Running the reaction in dichloromethane (DCM) at temperatures above its boiling point further increases the selectivity. Hence, the method of the present invention, by the slow addition of a substoichiometric amount of menthadienol to a mixture of olivetol and a metal triflate catalyst in DCM at a temperature above its boiling point, gives vastly improved selectivities for cannabidiol over its unwanted regioisomer over the prior art, and also significantly reduces the transformation of the cannabidiol into cyclized products.

Further, the cyclization of cannabidiol to delta-9-THC is a notoriously difficult reaction to control and carry out selectively. Previously, catalysts, such as $BF_3OEt_2$, have been used. These can induce isomerization of the desired delta-9 isomer to the thermodynamically more stable delta-8 isomer, which is very difficult to separate from the product. Moreover, cyclization of the phenol unit can occur onto the endocyclic double bond to give significant levels of iso-THC derivatives, which are also very difficult to remove. The method of the present invention, by using organoaluminum-based Lewis acid catalysts, gives vastly superior selectivities in this cyclization. For example, with $BF_3OEt_2$, yields of delta-9-THC are approximately 50-60% at best, with ca. 20% iso-THC and the inherent problem of isomerization of the delta-9-THC to the delta-8 isomer by the strong Lewis acid. Using $AlCl_3$ at very short reaction times, selectivities of ca. 10:1 delta-9-THC: iso-THC can be achieved, with little isomerization to delta-8 isomer. Extended reaction time favors the double bond isomerization. In contrast, when the method of the present invention is used as described herein, e.g., when $iBu_3Al$ is used, yields of delta-9-THC are >92% with <2% iso-THC with practically no isomerization of the desired product to delta-8-THC.

DETAILED DESCRIPTION OF THE INVENTION

The present invention relates to a process for preparation of a product compound of the formula:

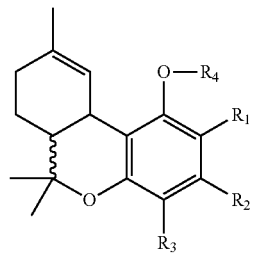

where:
$R_1$ is H, substituted or unsubstituted alkyl, carboxylic ester, or acyl;
$R_2$ is H, OH, protected hydroxyl, substituted or unsubstituted alkyl, alkenyl, alkynyl, acyl, aryl, or heteroaryl;
$R_3$ is H, substituted or unsubstituted alkyl, carboxylic ester, or acyl; and
$R_4$ is H, substituted or unsubstituted alkyl, silyl, hetero-substituted or unsubstituted acyl, alkylsulfonyl, arylsulfonyl, alkylphosphoryl, or arylphosphoryl.

The process involves treating a first intermediate compound of the formula:

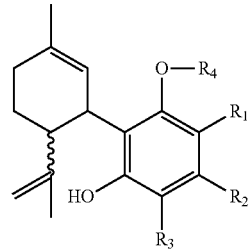

with an organoaluminum-based Lewis acid catalyst, under conditions effective to produce the product compound.

The organoaluminum-based Lewis acid catalyst used in the method of the present invention can be a trialkyl- or triarylaluminum, dialkyl- or diarylaluminum halide, alkylarylaluminum halide, dialkyl- or alkylaryl- or diarylaluminum alkoxide or aryloxide, dialkyl- or alkylaryl or diarylaluminum thioalkoxide or thioarylate, dialkyl- or alkylaryl or diarylaluminum carboxylate, alkyl- or arylaluminum dihalide, alkyl- or arylaluminum dialkoxide or diaryloxide or alkylaryloxide, alkyl- or aryl aluminum dithioalkoxide or dithioarylate, alkyl- or arylaluminum dicarboxylate, aluminum trialkoxide or triaryloxide or mixed alkylaryloxide, aluminum triacylcarboxylate or mixtures thereof. Suitable examples of organoaluminum-based Lewis acid catalysts include, but are not limited to, trimethylaluminum, triethylaluminum, triisopropylaluminum, triisobutylaluminum, trioctylaluminum, tridecylaluminum, diethylaluminum chloride, diisobutylaluminum chloride, diethylaluminum sesquichloride, ethyl aluminum dichloride, methylaluminum dichloride, isobutylaluminum dichloride, diethylaluminum ethoxide, diethylaluminum isopropoxide, diisobutylaluminum methoxide, diisobutylaluminum phenoxide, diphenylaluminum isopropoxide, tetraisobutylalumoxane, methylalumoxane, methylaluminum bis-(2,6-di-t-butyl-4-methylphenoxide), diisobutylaluminum acetate, diisobutylaluminum benzoate, diisobutylaluminum trifluoroacetate, diisobutylaluminum isopropoxide, diisobutylaluminum 2,6-di-t-butyl-4-methylphenoxide, isobutylaluminum bis-(2,6-di-t-butyl-4-methylphenoxide), isobutylaluminum diacetate, aluminum trimethoxide, aluminum triisopropoxide, aluminum tri-tert-butoxide, and aluminum trifluoroacetate. Several such catalysts are commercially available or can be prepared from commercially available aluminum reagents, using methods known in the literature, such as described by Ooi and Maruoka, *Science of Synthesis*, Vol. 7, pp. 131-195, Stuttgart, Germany: Thieme (2000), which is hereby incorporated by reference in its entirety.

In one embodiment of the present invention, the organoaluminum-based Lewis acid catalyst is a $C_1$-$C_{30}$ alkylaluminum-based or $C_6$-$C_{30}$ arylaluminum-based substance or mixture. In another embodiment of the present invention, the organoaluminum-based Lewis acid catalyst contains one or more oxygenated substituents bonded to the aluminum which modify the physical properties or performance of the catalyst. In another embodiment of the present invention, the organoaluminum-based Lewis acid catalyst may be made in situ before use by reaction of a precursor aluminum reagent with a modifying substituent. Specifically, the organoaluminum-based Lewis acid catalysts can be catalysts which provide high selectivity for delta-9-THC at lower levels of catalyst usage and at convenient rates for larger scale preparation. More specifically, the organoaluminum-based Lewis acid catalysts can be catalysts that produce delta-9-THC with very low levels of isomers (e.g., cis-delta-9-THC, delta-8-THC, and iso-THC), as these are difficult to remove from the product and render it difficult to achieve current standards of pharmaceutical purity.

In another embodiment of the present invention, the step of treating is carried out with the organoaluminum-based Lewis acid catalyst in an amount from about 0.5 mol % to about 100 mol % with respect to the first intermediate compound. In yet another embodiment of the present invention, the step of treating is carried out with the organoaluminum-based Lewis acid catalyst in an amount from about 5 mol % to about 15 mol % with respect to the first intermediate compound.

The step of treating can be carried out in an organic solvent. In one embodiment of the present invention, the solvent is aprotic. Examples of organic solvent include, but are not limited to, hexane, heptane, toluene, xylene, dichloromethane, and mixtures thereof.

The step of treating can be carried out at a temperature of from about −20° C. to about 100° C. In another embodiment of the present invention, the step of treating can be carried out at a temperature of from about −20° C. to about 50° C. In yet another embodiment of the present invention, the step of treating can be carried out at a temperature of from about 0° C. to about 30° C.

In another embodiment of the present invention, $R_2$ is n-$C_5H_{11}$ and $R_1$=$R_3$=$R_4$=H.

In another embodiment, the process of the present invention further involves reacting the product compound, where $R_4$=H, with a substituted or unsubstituted alkylsulfonyl halide, alkylsulfonyl anhydride, alkylsulfonyl mixed anhydride, alkylsulfonyl ester, or alkylsulfonic acid, under conditions effective to produce a second product compound of the formula:

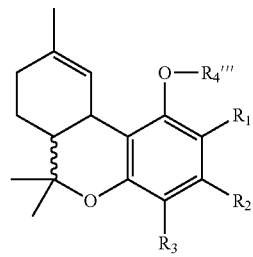

where:
$R_1$ is H, substituted or unsubstituted alkyl, carboxylic ester, or acyl;
$R_2$ is H, OH, protected hydroxyl, substituted or unsubstituted alkyl, alkenyl, alkynyl, acyl, aryl, or heteroaryl;
$R_3$ is H, substituted or unsubstituted alkyl, carboxylic ester, or acyl; and
$R_4'''$ is $SO_2R_5$, wherein $R_5$ is substituted or unsubstituted alkyl.

Alternatively, the product compound can be reacted with similar arylsulfonyl reagents to produce arylsulfonate compounds.

In one embodiment, the above reaction is carried out with an alkylsulfonyl compound in an amount from about 1 to about 1.5 equivalents with respect to the product compound at atmospheric pressure at a temperature of from about −20° C. to about 100° C. depending on the reagent. When alkylsulfonyl chloride is used, for example, the reaction is typically carried out at a temperature of from about −10° C. to about 20° C.

The product compound can be a totally synthetic substance or a naturally derived substance.

In another embodiment, the process of the present invention further involves carrying out a method selected from chromatography, countercurrent extraction, and distillation on the second product compound under conditions effective to produce a purified second product compound. In another embodiment, the process of the present invention further involves crystallizing the second product compound under conditions effective to produce a purified second product compound.

The purified second product compound can be hydrolyzed under conditions effective to produce the purified product compound in a desired isomer form. In another embodiment of the present invention, the step of hydrolyzing is carried out in the presence of an organic or inorganic base in a solvent. Examples of base include, but are not limited to, sodium hydroxide, potassium t-butoxide, and mixtures thereof.

Examples of solvent include, but are not limited to, methanol, ethanol, isopropanol, t-butanol, acetonitrile, and mixtures thereof.

In another embodiment of the present invention, $R_1=R_3=H$ and $R_2$ is H, OH, protected hydroxyl, substituted or unsubstituted alkyl, alkenyl, alkynyl, acyl, aryl, or heteroaryl. In yet another embodiment of the present invention, $R_1=R_3=H$ and $R_2$ is n-$C_5H_{11}$.

In another embodiment of the present invention, the second product compound is of the formula:

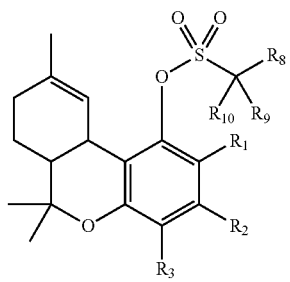

where:
$R_8$, $R_9$, and $R_{10}$ are the same or different and independently selected from the group consisting of H, substituted or unsubstituted alkyl, substituted or unsubstituted aryl, substituted or unsubstituted heteroaryl, or halo; and
$R_8$ and $R_9$; $R_8$ and $R_{10}$; or $R_9$ and $R_{10}$; or $R_8$, $R_9$, and $R_{10}$ can together result in the formation of a cyclic moiety.

"Alkyl" is defined herein as $C_1$-$C_n$, wherein the carbon chains may be straight, branched, or containing or comprising rings. "Substituted alkyl" is defined as $C_{1X}$-$C_nX$ as described above, except that the carbons may bear one or more substituents X, such as functional groups containing oxygen, nitrogen, sulfur, halogen or aromatic or heteroaromatic rings. "Aryl" is defined as $C_6$-$C_n$ aromatic rings or multiple rings. "Substituted aryl" is defined as $C_6$-$C_n$ aromatic rings or multiple rings bearing substituents on one or more of these rings which may be functional groups of carbon, oxygen, nitrogen, sulfur or halogen. "Heteroaryl" is defined as aromatic rings containing one or more heteroatom within the ring or rings. "Substituted heteroaryl" is defined as heteroaryl containing one or more substituents on one or more ring which may be functional groups of carbon, oxygen, nitrogen, sulfur or halogen. "Halo" is defined as chlorine, bromine, iodine or fluorine. Further, $R_8$, $R_9$, and $R_{10}$ may contain chiral centers or define a chiral center on the carbon bearing them.

In another embodiment of the present invention, the second product compound is a straight chain alkylsulfonate selected from methanesulfonate, ethanesulfonate, propanesulfonate, butanesulfonate, pentanesulfonate, hexanesulfonate, heptanesulfonate, octanesulfonate, nonanesulfonate, decanesulfonate, undecanesulfonate, dodecanesulfonate, tridecanesulfonate, tetradecanesulfonate, pentadecanesulfonate, hexadecanesulfonate, heptadecanesulfonate, octadecanesulfonate, nonadecanesulfonate, and icosanesulfonate.

In another embodiment of the present invention, the second product compound is a branched chain alkylsulfonate selected from cyclopropylsulfonate, isopropylsulfonate, isobutylsulfonate, tert-octylsulfonate, adamantly sulfonate, and 10-camphorsulfonate.

In another embodiment of the present invention, the second product compound is a substituted alkylsulfonate selected from chloromethylsulfonate, 2-chloroethylsulfonate, trifluoromethylsulfonate, trifluorethylsulfonate, perfluoroethylsulfonate, perfluorobutylsulfonate, perfluorooctanesulfonate, 2-aminoethylsulfonate, 2-dimethylaminoethylsulfonate, 2-phthalimidoethylsulfonate, 2-morpholinoethylsulfonate, 3-morpholinopropylsulfonate, 4-morpholinobutylsulfonate, 2-N-piperidinylethylsulfonate, 3-N-piperidylpropylsulfonate, 2-pyrrolidinylmethylsulfonate, 2-methoxyethylsulfonate, (1R)-3-bromocamphor-8-sulfonate, (1S)-3-bromocamphor-8-sulfonate, (1S)-3-bromo-camphor-10-sulfonate, (1R)-10-camphorsulfonate, and (1S)-10-camphorsulfonate.

Specifically, the second product compound can have the following formula, where the camphorsulfonate group is in the S configuration:

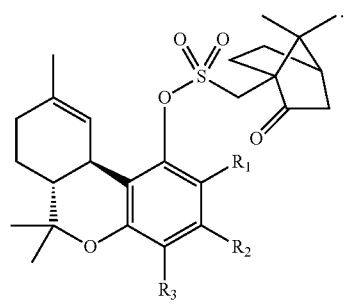

Alternatively, the second product compound can have the following formula, where the camphorsulfonate group is in the R configuration:

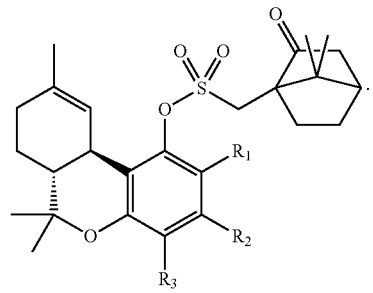

In another embodiment of the present invention, the second product compound is a diastereomeric mixture of the following two formulae, where the camphorsulfonate group is in the S and R configurations, respectively:

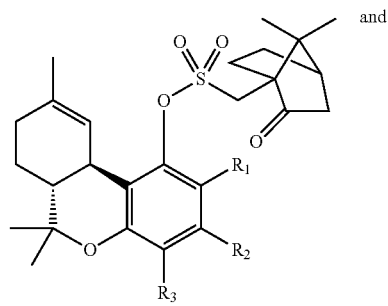

-continued

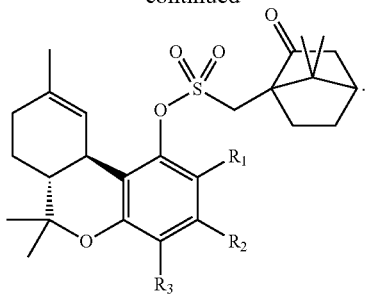

In another embodiment of the present invention, the second product compound is an aryl or heteroaryl substituted alkylsulfonate selected from benzylsulfonate, 2-nitrobenzylsulfonate, 3-nitrobenzylsulfonate, 4-nitrobenzylsulfonate, 2-chlorobenzylsulfonate, 3-chlorobenzylsulfonate, 4-chlorobenzylsulfonate, 2-trifluoromethybenzylsulfonate, 3-trifluoromethylbenzylsulfonate, 4-trifluoromethylbenzylsulfonate, 3,5-dichlorobenzylsulfonate, 3,5-ditrifluoromethylbenzylsulfonate, 4-methylbenzylsulfonate, 4-t-butylbenzylsulfonate, 1-napthylethylsulfonate, 2-pyridylmethylsulfonate, 3-pyridylmethylsulfonate, 4-pyridylmethylsulfonate, 2-(2-pyridyl)ethylsulfonate, and diphenylmethanesulfonate.

In another embodiment, the process of the present invention further involves reacting a second intermediate compound of the formula:

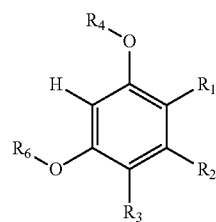

where:
$R_6$ is H, substituted or unsubstituted alkyl, silyl, hetero-substituted or unsubstituted acyl, alkylsulfonyl, arylsulfonyl, alkylphosphoryl, or arylphosphoryl;
with a second compound of the formula:

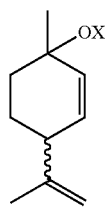

where X=H, alkyl, acyl, silyl, aryl, heteroaryl, sulfinyl, sulfonyl, phosphoryl, or phosphinyl, in the presence of a metal triflate catalyst, under conditions effective to form the first intermediate compound.

In one embodiment of the present invention, the step of reacting is carried out under conditions effective to achieve preferential formation of the first intermediate compound over undesired stereochemical and regiochemical isomers as well as other impurities.

In another embodiment of the present invention, $R_1$ is H or $COOR_7$, $R_2$ is n-$C_5H_{11}$, and $R_3$ is H or $COOR_7$, where $R_7$ is $C_1$-$C_{20}$ alkyl. In another embodiment of the present invention, $R_1$ is $COOR_7$, where $R_7$ is ethyl, $R_2$ is n-$C_5H_{11}$, and $R_3$ is H or $COOR_7$, where $R_7$ is $C_1$-$C_{20}$ alkyl, $R_4$=H, and X=H. In yet another embodiment of the present invention, $R_1$=$R_3$=$R_4$=H, $R_2$=n-$C_5H_{11}$, and X=H.

In another embodiment, the above reaction is carried out with the second intermediate compound in an amount of from about 1 to 1.2 equivalents with respect to the second compound.

The metal triflate catalyst can be a transition metal triflate or lanthanide triflate. Examples of transition metal triflate include, but are not limited to, zinc triflate, ytterbium triflate, yttrium triflate, and scandium triflate. Specifically, the transition metal triflate is zinc triflate or scandium triflate.

In another embodiment of the present invention, the step of reacting is carried out with the metal triflate catalyst in an amount from about 0.5 mol % to about 100 mol % with respect to the second intermediate compound. In yet another embodiment of the present invention, the step of reacting is carried out with the metal triflate catalyst in an amount from about 0.5 mol % to about 10 mol % with respect to the second intermediate compound.

In another embodiment of the present invention, the step of reacting is carried out in an organic solvent. Examples of organic solvent include, but are not limited to, a hydrocarbon, aromatic hydrocarbon, halogenated hydrocarbon, ether, ester, amide, nitrile, carbonate, alcohol, carbon dioxide, and mixtures thereof. Specifically, the organic solvent is dichloromethane.

In another embodiment of the present invention, the step of reacting is carried out at a temperature of from about −20° C. to about 150° C. Specifically, the step of reacting can be carried out under pressure at a temperature above the normal atmospheric boiling point of the organic solvent or where temperatures are above boiling point and pressure is above atmosphere.

In another embodiment of the present invention, the step of reacting is carried out with a less than about one equivalent of the second compound to the second intermediate compound.

EXAMPLES

The following examples are provided to illustrate embodiments of the present invention but are by no means intended to limit its scope.

Example 1

Preparation of Ethyl Cannabidiolate by Condensation of Ethyl Olivetolate with Menthadienol Ethyl olivetolate (25 g, 99 mmol) was dissolved in dichloromethane (250 mL) and $MgSO_4$ (25 g, 1 wt) and $Sc(OTf)_3$ (4.88 g, 9.9 mmol, 10 mol %) were added sequentially. A solution of menthadienol (24.5 g, 161 mmol, 1.6 equiv, assuming purity of 100% but really approximately 80-85% AUC by GC) in dichloromethane (125 mL) was added over 1.5 h using a dropping funnel The reaction was monitored by HPLC analysis and after approximately 3 h the reaction was filtered through celite, the solids washed with dichloromethane (125 mL), and the combined organics were evaporated under reduced pressure. The residue was dissolved in heptane and applied to 5 wt silica, then eluted with heptane (1×500 mL), 10% dichloromethane/heptane (6×500 mL), 15% dichloromethane/heptane (2×500 mL) and 20% dichloromethane/heptane (2×500 mL). Fractions containing ethyl cannabidiolate were combined and concentrated to give the product (31.3 g, 82% yield, with a purity of 93.3% AUC by HPLC).

Example 2

Preparation of Cannabidiol

The ethyl cannabidiolate from Example 1 (31.3 g, 81 mmol) was dissolved in MeOH (10 vol, 310 mL) and degassed with argon. Separately, a solution of NaOH (64.8 g, 1.62 mol, 20 equiv) in deionized water (10 vol, 310 mL) was prepared and degassed with argon. The organic solution was added to the aqueous solution under a strict argon atmosphere, then the mixture heated to reflux and held there for 3.5 h, then cooled to room temperature. HPLC analysis indicated completion of reaction. The reaction mixture was quenched with aqueous citric acid (129.6 g citric acid, 8.3 equiv, as a 30% solution in water). The addition was exothermic. Heptane (310 mL, 10 vol) was added to the mixture and the product extracted into the heptane phase. A second extraction using heptane (150 mL, ca. 5 vol) was then performed and HPLC analysis of the aqueous fractions indicated the absence of the cannabidiol. The combined organics were dried by azeotropic distillation of the water and concentrated to ca. 250 mL and then cooled to −16 to −17° C., and seeded with solid cannabidiol when the temperature reached −1.5° C. After 20 h, the resulting solids were filtered off, washed with cold heptane and dried on the filter, then under high vacuum. This ultimately gave 17.9 g cannabidiol (57.5% yield over two steps from ethyl olivetolate) with a purity of >99.8% AUC by HPLC.

Example 3

Preparation of Trans-delta-9-THC

The cannabidiol from Example 2 (18.5 g, 58.8 mmol) was dissolved in dichloromethane (324 mL, 17.5 vol) and heated to 25° C. Triisobutylaluminum (5.9 mL of 1 M solution in hexane, 10 mol % catalyst) was then added via syringe and the reaction stirred at 20-25° C. for approx 20 h. After this time, HPLC analysis of the reaction mixture showed consumption of the cannabidiol and 94.8% trans-delta-9-THC. The reaction was quenched with water (1.6 mL, 15 equiv. based on moles of catalyst) and stirred for 1 h. After filtration through celite, the solvent was switched to toluene and the reaction mixture azeotroped to remove any remaining water. The solution of product in toluene (total volume ca. 92 mL) was used directly in the subsequent step.

Example 4

Preparation of Trans-delta-9-THC 3-Nitrobenzenesulfonate

The crude toluene solution of trans-delta-9-THC (assumed to be quantitative yield, 58.8 mmol) from Example 3 was treated with triethylamine (24.6 mL, 3 equiv) and then a solution of 3-nitrobenzenesulfonyl chloride (13.04 g, 1 equiv) in toluene (92.5 mL) was added to the reaction at room temperature over approximately 30 min. The addition funnel was washed with toluene (10 mL) which was added to the reaction. After 2 h, the starting material was consumed (by HPLC analysis) and the reaction was quenched with water (185 mL) and stirred for 20 min. The organic phase was collected and then washed with 10% citric acid (95 mL), saturated NaHCO$_3$ solution (95 mL) and water (185 mL) then azeotropically dried. The solvent was replaced with isopropanol (147 mL, 5 vol based on 100% yield of sulfonate), seeded with crystalline trans-delta-9-THC 3-nitrobenzenesulfonate and stirred at room temperature for 24 h. The resulting solids were isolated by filtration to give 19.4 g trans-delta-9-THC 3-nitrobenzenesulfonate with an HPLC purity of 99.2% (AUC). A second crystallization from isopropanol (5 vol) was performed to give 16.7 g product with a purity of 99.6% AUC by HPLC. Yield from cannabidiol: 57.4%.

Example 5

Preparation of (−)-Trans-delta-9-THC

Trans-delta-9-THC 3-nitrobenzenesulfonate (16.5 g) was dissolved in acetonitrile (330 mL, 20 vol) and 0.5 M NaOH (165 mL, 10 vol) was added. The mixture was heated to reflux and, after ca. 2 h, HPLC analysis indicated that the reaction was complete. After cooling, water (500 mL, 30 vol) was added followed by heptane (165 mL, 10 vol). The phases were mixed and the heptane layer was collected. The aqueous phase was extracted again with heptane (165 mL, 10 vol) and the organic extracts were combined, washed with water (165 mL, 10 vol), dried over Na$_2$SO$_4$, filtered, and concentrated to a dark brown-purple oil. The oil was reconstituted with EtOH and restripped to give the product as a light brown oil (10.79 g), containing ca. 6% EtOH by proton NMR analysis. HPLC analysis indicated a purity of 99.66% AUC.

Example 6

Preparation of Cannabidiol by Condensation of Olivetol with Menthadienol

A solution of olivetol (1 g, 5.56 mmol) in dichloromethane (15 mL) was treated with Zn(OTf)$_2$ (10 mg, 0.5 mol %) and heated to 60° C. in a modified pressure tube equipped with a septum for additions. A solution of menthadienol (0.63 g, 0.75 equiv, 4.14 mmol) in dichloromethane (5 mL) was added via syringe over 5.5 h. HPLC analysis of the reaction after a total of 6 h showed a 2.6:1 ratio of cannabidiol to abn-cannabidiol (47.0%:17.9%) with 23.3% unreacted olivetol and 4.3% of a double addition product. Only trace levels of cyclized degradants (delta-8- and delta-9-THC) were observed, even after continuation of the heating for a total of 20 h.

Example 7

Preparation of (+)-Menthadienol

To a stirred mixture of potassium carbonate (2.98 kg) in ethanol (16.7 L) was added (+)-limonene oxide (25.0 kg) and the mixture heated to 60° C. Thiophenol (8.86 kg) was added over 11 hours at 70-80° C. Ethanol was distilled out at atmospheric pressure over the course of four hours until the pot temperature reached 105° C., the batch cooled to 80° C. then cold water (16 L) added. After cooling to 40° C., methyl t-butyl ether (MTBE, 16 L) was added. The organic phase was separated, washed with water (4.5 L), and the solvents removed under reduced pressure at 60° C. The residual oil (30.9 kg) was fed to a 4 inch, wiped-film evaporator at 3 mm and 145° C. to remove the unreacted limonene oxide. The non-volatile fraction (14.7 kg of thiophenyl ether) was dissolved in glacial acetic acid (26.0 L) and stirred while 35% hydrogen peroxide (6.0 kg) added over 6.5 hours. The reaction temperature was maintained at 10-20° C. The reaction was allowed to warm to room temperature overnight, then transferred into a mixture of warm water (89 L, 40-45° C.) and MTBE (34 L). The organic phase was washed aqueous 5% sodium bicarbonate (4 washes, 18 L each) at 40-45° C., to achieve a final pH of ca. 8 and a negative starch-iodine test. The organic phase was concentrated under reduced pressure at 60° C. to obtain a residue of crude sulfoxide mixture (14.8 kg, estimated 95% yield). This residual was dissolved in tetraglyme (11.6 L) and stored until needed, during this time the product partially crystallized. The solution was gently warmed to redissolve the sulfoxide mixture. To a portion of this tetraglyme solution (containing ca. 8.3 kg of sulfoxide mixture) was added potassium carbonate (2.7 kg) and tetraglyme (5 L) and the stirred mixture was heated to 180° C. with application of vacuum (75-80 mm), distilling the volatiles over the course of nine hours. The strong smelling distillate (ca. 2.8 kg) was dissolved in heptane (2.5 L) and washed with water (4.5 L+1 L), then concentrated under reduced pressure at 60° C. to crude (+)-menthadienol (1.76 kg) of approximately 83% purity by GC. Several batches of crude (+)-menthadienol (totaling ca. 6.68 kg) were combined with hexadecane (1.00 kg) and solid potassium carbonate (67 grams) in a stirred round bottom flask fitted with a 5 plate 2 inch diameter Oldershaw column fitted with a reflux return splitter. Distillation was effected at pot temperature of ca. 105-110° C. with vacuum of ca. 1-5 mm. After the initial low boiling fractions were removed (bp: 45-75° C.), main fractions of boiling point: 75-80° C. were collected totaling 4.0 kg of (+)-menthadienol (assayed at 95-98% by gas chromatography (AUC)). Optical rotation of a sample prepared by this procedure was +75.4° (c=1.074 in chloroform at 25° C.). The literature value is +67.9° at 20° C. (Ohloff et al., *Helvetica Chimica Acta*, 63:76 (1980), which is hereby incorporated by reference in its entirety).

Example 8

Representative Lab Procedures for Ethyl Olivetolate

Preparation of Sodium Ethyl Dihydroolivetolate

To a stirred mixture of anhydrous ethanol (10.5 L) and diethylmalonate (1.90 kg) at 20° C. was added, over 35 minutes, a sodium ethoxide solution (21% in ethanol, 4.2 L). The reaction temperature was allowed to rise to 27° C. To the resulting slurry was added 3-nonene-2-one (1.50 kg), over the course of three hours, allowing the temperature to rise to 45-50° C. The reaction mixture heated to 70° C. over two hours and held for an additional two hours. The reaction mixture was then cooled to 0° C. and held overnight. The solid product was then collected by filtration through a polypropylene filter. The solid cake was rinsed with MTBE (5.0 L) then dried under reduced pressure at 20-25° C. to constant weight affording 2.38 kg (99% yield) of sodium ethyl dihydroolivetolate as an off-white solid. $^1$H NMR 500 MHz (DMSO-$d_6$) δ 0.85 (t, 3H), 1.1-1.5 (m, 11H), 1.7 (dd, 1 H), 2.05, dd, 1 H), 2.4 (m, 1 H), 2.7 (d, 1 H), 4.05 (q, 2 H) and 4.4 ppm (s, 1 H). HPLC analysis showed 100% product (Phenomenex (Houston, Tex.) HyperClone 5 u BDS C18 column, 4.6×150 mm, 1 mL/min, gradient 100% water/0.1% TFA to 100% acetonitrile/0.1% TFA over 15 minutes, rt=8.0 min).

Preparation of Ethyl Dibromoolivetolate

To a stirred suspension of sodium ethyl dihydroolivetolate (200.8 g, 0.727 mol) and anhydrous sodium acetate (238.5 g, 2.91 mol) in acetic acid (1010 mL) at 50° C. was dropwise added bromine (655.5 g, 2.29 mol) over the course of three hours while maintaining the batch temperature at 50-55° C. After stirring an additional hour at 50-55° C., the slurry was cooled over three hours to 20° C. Water (925 mL) was added over 1 h during which the product crystallized. The slurry was cooled to 10° C., held overnight, and then filtered through filter paper. The solid cake was washed with water (3×400 mL, to achieve a final rinse pH of 4) and then air dried overnight to obtain 310 g (86% yield) of crude ethyl dibromoolivetolate, containing ca. 11.7% by weight of water. $^1$H NMR, 500 MHz (CDCl$_3$) δ 0.9 (t, 3H), 1.4 (m, 8H), 1.6 (t, 3H), 3.1 (m, 2H), 4.4 (m, 2H), 6.4 (s, 1H) and 12.3 ppm s, 1H). HPLC analysis showed 98.5% product (AUC, Sunfire reversed phase C18 column from Waters Corporation (Milford, Mass.), 4.6×150 mm, 1 mL/min, gradient 80% 0.1% TFA in water with 20% 0.5% TFA in acetonitrile to 100% of 0.5% TFA in acetonitrile over 15 minutes, rt=13.8 min).

Preparation of Ethyl Olivetolate

A 2 L Parr reactor charged with ethyl dibromoolivetolate (160.3 g of water wet material, 0.345 mol), ethanol (290 mL), water (440 mL), sodium citrate (220 g, 0.747 mol) and 5% palladium-on-charcoal catalyst (7.4 g) was degassed with nitrogen and then pressurized to 50 psig with hydrogen gas. The stirrer was started and the reaction mixture was heated to 60° C. and maintained at that pressure and temperature for six hours after which the heat was turned off. After cooling to ambient temperature, the mixture was filtered through celite (100 g) and the reactor and solid filter cake was rinsed with water (600 mL), then toluene (300 mL). The layers were separated and the organic phase was evaporated under reduced pressure to a semisolid residue. Heptane (260 mL) was added and the mixture was warmed to 45° C. at which point the solids dissolved. The stirred mixture was allowed to cool slowly to ambient temperature overnight, during which crystallization occurred. The slurry was cooled to 5° C., held 4 hours, and the solid product was collected by filtration. The filter cake was rinsed with cold heptane (150 mL) then dried to a constant weight under reduced pressure at 20° C. to afford 63.0 g (72% yield) of yellow crystals of ethyl olivetolate. HPLC analysis indicated that the product was 99.6% pure (AUC, Sunfire reversed phase C18 column, 4.6×150 mm, 1 mL/min flow rate, gradient 80% 0.1% TFA in water with 20% 0.5% TFA in acetonitrile to 100% of 0.5% TFA in acetonitrile over 15 minutes, rt=10.3 min) This product was identified by melting point (mp: 66-67° C., literature: 68° C., Anker et al., *J. Chem. Soc.* pp. 311 (1945)) and NMR analysis. $^1$H NMR, 500 MHz (CDCl$_3$) δ 0.9 (t, 3H), 1.4 (m, 8H), 1.6 (t, 3H), 2.8 (m, 2H), 4.4 (m, 2H), 5.4 (br s, 1 H), 6.2 (s, 1H), 6.3 (s, 1H) and 11.8 ppm (s, 1H).

Example 9

Preparation of Ethyl Cannabidiolate

To a stirred solution of ethyl olivetolate (40.1 g, 155 mmol) in dichloromethane (360 mL) was added anhydrous magnesium sulfate (10.4 g) and scandium triflate (3.93 g, 8 mmol). The mixture was cooled to 10° C. To this slurry was added a cold solution of (+)-menthadienol (25.1 g, 155 mmol) in dichloromethane (160 mL) over three minutes, followed by a dichloromethane rinse (120 mL). A slight exotherm was observed. After stirring at 10° C. for three hours, HPLC analysis showed the reaction was complete by no further decrease in the olivetolate ester concentration. The reaction was quenched by addition of solid anhydrous sodium carbonate (4.0 g) and stirred overnight at 25° C. The reaction mixture was clarified by filtration through a bed of celite and the flask and filter cake was washed with dichloromethane (250 mL). The combined filtrates were concentrated under reduced pressure to about 150 mL of volume. Heptane (400 mL) was added and the mixture was again concentrated under reduced pressure to about 150 mL. Heptane (400 mL) was added and the mixture extracted with aqueous sodium hydroxide solution (2×200 mL of a 20% aqueous solution) followed by water (2×200 mL). HPLC analysis showed the organic phase to be free of any residual ethyl olivetolate. The heptane phase was concentrated under reduced pressure to 58.6 g (87% yield after correcting for the HPLC purity of 90%) of a dark colored oil, primarily ethyl cannabidiolate as determined by HPLC analysis. This crude material is used directly in the next step described in Example 9.

Example 10

Preparation of Cannabidiol

Crude ethyl cannabidiolate (58.6 g, ca. 90% pure by HPLC) was dissolved in methanol (390 mL) and the stirred solution was degassed by refluxing under nitrogen for 1 hour. Aqueous sodium hydroxide solution (80.8 g of NaOH in 390 mL of water) was degassed by refluxing under nitrogen for one hour. The hydroxide solution was transferred under nitrogen pressure, through a steel cannula to the hot ethyl cannabidiolate/methanol solution over 20 minutes while maintaining the reaction at 70° C. After five hours at 70-80° C., the hydrolysis was found complete by HPLC analysis and the reaction cooled to 20° C. The reaction was quenched by addition of a degassed aqueous solution of citric acid (50 wt % solution, 400 g). The mixture was extracted with heptane (400 mL) and the organic layer was washed with aqueous sodium bicarbonate solution (300 mL) and water (300 mL). The heptane solution was concentrated under reduced pressure to ca. 100 mL, reconstituted with heptane (400 mL), concentrated again to ca. 50 mL and heptane (200 mL) was added. The slowly stirred heptane solution was cooled to 10° C., seeded with cannabidiol crystals and stirred slowly at 10° C. for three hours to develop a crop of crystals. The slurry was stored overnight at −5° C. The solid product was collected by filtration on cold sintered glass and the reactor and cake rinsed with cold heptane (150 mL). The solids were dried under nitrogen stream for two hours then under reduced pressure at 20° C. for 15 hours to afford 21 g (44% yield) of solid cannabidiol. HPLC analysis showed 99.6% (AUC) product (Sunfire C18 5 u column, 4.6 mm×150 mm, 1 ml/min flow rate, gradient 80% of 0.1% TFA/water and 20% 0.05% TFA/acetonitrile to 100% 0.05% TFA/acetonitrile over 15 minutes, rt=11.9 min).

Example 11

Preparation of Crude Delta-9-Tetrahydrocannabinol

To a nitrogen inerted, stirred solution of cannabidiol (21.2 g, 67.1 mmol) in dichloromethane (370 mL) was added, by syringe pump, commercial tri-isobutylaluminum solution (1 M in hexanes, 6.7 mL, 10 mol %) over 4.5 hours. The temperature of the reaction mixture was maintained at 20-25° C. and the mixture was stirred overnight. Additional charges of triisobutylaluminum solution (1 M in hexanes, 2.67 mL added, 4 mol %) were made over the next day to drive the reaction to >99% conversion by HPLC analysis. The reaction was quenched by addition of water (250 mL), stirred 30 minutes, combined with a slurry of celite in dichloromethane (10.0 g in 70 mL dichloromethane) and then clarified. The reactor and filter cake were rinsed with dichloromethane (50 mL) and the combined filtrates distilled under reduced pressure (25° C. pot temperature, 22 inches of vacuum) to about 50 mL volume. Toluene (106 mL) was added and the solvents again removed under reduced pressure. More toluene (106 mL) was added and removed under reduced pressure and then the dichloromethane-free residue was reconstituted in toluene (100 mL). HPLC analysis showed 95.6% delta-9-tetrahydrocannabinol, 1.1% cis-tetrahydrocannabinol, and no cannabinol. (Sunfire C18 5 u, 4.6 mm×150 mm, 1 ml/min, gradient 80% 0.1% TFA/water and 20% 0.05% TFA/acetonitrile to 100% 0.05% TFA/acetonitrile over 15 minutes, delta-9 tetrahydrocannabinol: rt=15.1 min). The yield was estimated at 95%. The solution was stored under nitrogen until needed for preparation of the camphorsulfonate derivative.

Example 12

Preparation of Delta-9-Tetrahydrocannabinol (1S)-10-Camphorsulfonate

To a solution of crude delta-9-tetrahydrocannabinol in toluene (containing 21.1 g of delta-9-tetrahydrocannabinol, 67.1 mmol on 100 mL of toluene) was added a solution of 4-dimethylaminopyridine (0.83 g) and diisopropylethylamine (35.2 mL, 3 equiv) in toluene (106 mL). The stirred reaction mixture was cooled to 0° C. and a slurry of (1S)-10-camphorsulfonyl chloride (19.8 g, 74.8 mmol, 1.1 equiv.) in toluene (150 mL) at 0° C. was added over 30 minutes. The addition funnel rinsed with toluene (50 mL) and this rinse was added to the stirred reaction mixture, and the mixture held overnight at 0° C. Additional (1S)-10-camphorsulfonyl chloride (total of 10.75 g in toluene (55 mL)) was added over six hours to achieve 99% conversion. Water (200 mL) was added over 15 minutes and the mixture stirred overnight. The organic phase was washed with 5% aqueous citric acid solution (100 mL), 5% aqueous sodium bicarbonate solution (100 mL) and 5% aqueous sodium chloride solution (100 mL). The toluene layer was concentrated under reduced pressure to about 100 mL and additional toluene (100 mL) was added. This drying sequence was repeated and then the solvent was replaced with isopropanol (200 mL). The isopropanol was concentrated under reduced pressure and the residue was suspended in isopropanol (200 mL). The slurry was warmed to 40° C. at which point the solids dissolved. The stirred solution was cooled to 20° C. over 4 hours during which the product crystallized. After stirring for 2 h at 15-20° C., the product was collected by filtration, rinsed with cold isopropanol (90 mL), and the solid crystalline product was dried under reduced pressure at 50° C. overnight to afford 19.67 g (56% yield) of delta-9-tetrahydrocannabinol (1S)-10-camphorsulfonate. HPLC analysis showed 98.5% delta-9-tetrahydrocannabinol (1S)-10-camphorsulfonate, 0.86% delta-8-tetrahydrocannabinol (1S)-10-camphorsulfonate, and 0.35% cis-tetrahydrocannabinol (1S)-10-camphorsulfonate. mp 94-95° C. $^1$H NMR 500 MHz (CDCl$_3$) δ 0.9 (s, 3H), 1.1 (s, 3H), 1.2 (s, 3H), 1.35 (m, 4 H), 1.4-1.5 (m, 5H), 1.45-1.55 (m, 5H), 1.95 (s, 1H), 2.0 (s, 1H), 2.05-2.2 (m, 4H), 2.40 and 2.45 (d of t, 1H), 2.45-2.60 (m, 3H), 3.25 (d, 1H), 3.42 (d, 1H), 3.88 (d, 1H), 6.17 (s, 1H), 6.6 (s, 1H) and 6.68 ppm (s, 1H).

Example 13

Purified Delta-9-Tetrahydrocannabinol

To a mechanically stirred slurry of crystalline purified delta-9-tetrahydrocannabinol (1S)-10-camphorsulfonate (1.1 g, 2.1 mmol) in water (3.6 mL) and t-butanol (7.4 mL) under argon, was added a mixture of sodium hydroxide (0.83 g, 21 mmol) in water (7.4 mL) and t-butanol (15 mL). The slurry was heated to 70° C. over 2 h, at which point the HPLC analysis showed the hydrolysis to be complete. The reaction mixture was cooled to ambient temperature and diluted with water (11 mL) and extracted with heptane (11 mL). The heptane solution was washed with water (2×6 mL). The heptane solution was concentrated under reduced pressure and the residue was dissolved in ethanol (5 mL). The ethanol solution was filtered through a 0.45 micron filter. HPLC analysis showed 99.2% delta-9-tetrahydrocannabinol and 0.49% cis-delta-9-tetrahydrocannabinol. (Agilent Technologies (Wilmington, Del.) Hypersil Gold, 4.6 mm×150 mm, isocratic MeOH/H$_2$O/THF (71:24:5) mixture at 1 mL/min flow rate, 228 nm, delta-9-tetrahydrocannabinol rt=18.9 min, cis-delta-9-tetrahydrocannabinol rt=17.7 min). This solution was stored under an argon atmosphere and in the freezer until it was carried into the next step.

Example 14

Preparation of Delta-9-Tetrahydrocannabinol in Sesame Oil

A stock solution of delta-9 THC in ethanol (6.90 g of 0.109 mg/mL tetrahydrocannabinol concentration) was mixed with Croda high purity sesame oil (29.25 g) from Croda, Inc. (Edison, N.J.). The resulting solution was warmed to 30° C., and sparged with filtered argon for 24 hours to afford ca. 30 g of 2.5% delta-9-tetrahydrocannabinol in sesame oil. $^1$H NMR 500 MHz (CDCl$_3$) showed no residual ethanol.

Example 15

Preparation of Crude Delta-9-Tetrahydrocannabinol

To a solution of cannabidiol (500 mg) in dichloromethane (8.75 mL) at 20° C., was added a solution of an organoaluminum-based Lewis acid catalyst in dichloromethane (1.0 mL) over five minutes and the reaction mixtures stirred under nitrogen and monitored by HPLC. Table 1 below shows the relative HPLC quantitation of the different product compounds in area percent at the time specified, using different organoaluminum-based Lewis acid catalysts.

TABLE 1

| Organoaluminum-based Lewis Acid Catalyst | Relative HPLC Quantitation of Product Compounds (in area percent) | | | | | |
|---|---|---|---|---|---|---|
| | Reaction Time | Cannabidiol | cis-THC | 9-THC | 8-THC | iso-THC |
| 20 mol % triisobutylaluminum | 21 h | 9.8 | 1.8 | 87.6 | 0.3 | 0.5 |
| 20 mol % isobutylaluminum-bis-(2,6-di-t-butyl-4-methylphenoxide) | 22 h | 3.3 | 3.4 | 91.5 | 0.5 | 0.7 |
| 20 mol % diisobutylaluminum thiophenoxide | 69 h | 3.5 | 3.7 | 89.6 | 1.2 | 1 |
| 20 mol % diisobutylaluminum benzoate | 22 h | 6.3 | 2.7 | 92.5 | 0.5 | 0.7 |
| 20 mol % diisobutylaluminum acetate | 22 h | 5.1 | 2.6 | 91.3 | 0.4 | 0.6 |
| 20 mol % aluminum tri-t-butoxide | 22 h | 70.5 | 0.3 | 29 | 0.0 | 0.1 |

Although the invention has been described in detail, for the purpose of illustration, it is understood that such detail is for that purpose and variations can be made therein by those skilled in the art without departing from the spirit and scope of the invention which is defined by the following claims.

What is claimed:
1. A process for preparation of a product compound of the formula:

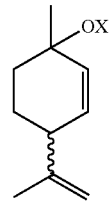

wherein X=H, alkyl, acyl, silyl, aryl, heteroaryl, sulfinyl, sulfonyl, phosphoryl, or phosphinyl;
said process comprising:
treating a first intermediate compound of the formula:

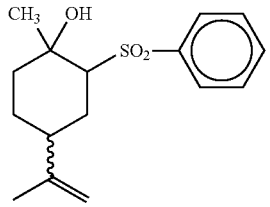

with a carbonate base under conditions effective to produce the product compound.
2. The process according to claim 1, wherein the carbonate base is K$_2$CO$_3$.
3. The process according to claim 1, wherein X is hydrogen.
4. The process according to claim 1 further comprising:
reacting a starting material compound of the formula:

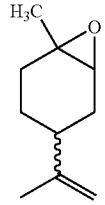

under conditions effective to form a second intermediate compound of the formula:

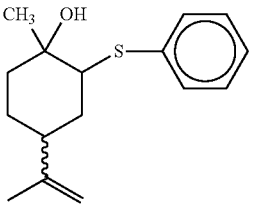

and,
reacting the second intermediate compound under conditions effective to form the first intermediate compound.
5. The process according to claim 4, wherein the conditions effective to form the second intermediate compound include reacting the starting material compound with thiophenol.

* * * * *

UNITED STATES PATENT AND TRADEMARK OFFICE
CERTIFICATE OF CORRECTION

PATENT NO.      : 8,106,244 B2
APPLICATION NO. : 13/108651
DATED           : January 31, 2012
INVENTOR(S)     : David C. Burdick et al.

It is certified that error appears in the above-identified patent and that said Letters Patent is hereby corrected as shown below:

In claim 1, column 20, line 22, the formula

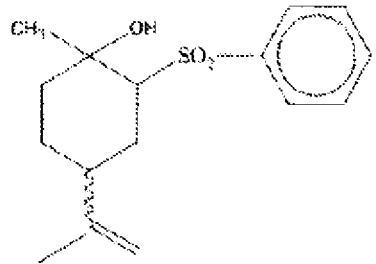

should be replaced with

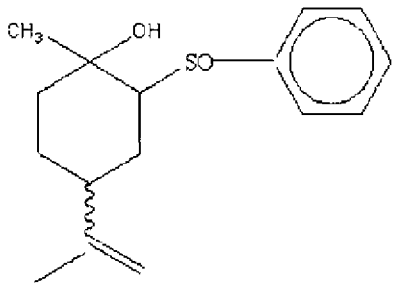

Signed and Sealed this
Nineteenth Day of March, 2013

Teresa Stanek Rea
*Acting Director of the United States Patent and Trademark Office*